US012564491B2

(12) United States Patent
Senesh et al.

(10) Patent No.: US 12,564,491 B2
(45) Date of Patent: Mar. 3, 2026

(54) MULTI-LAYER COVERING FOR A PROSTHETIC HEART VALVE

(71) Applicant: Edwards Lifesciences Corporation, Irvine, CA (US)

(72) Inventors: Gil Senesh, Adi (IL); Jeanette Jasmine Corona Kelly, Anaheim, CA (US); Sandip Vasant Pawar, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 606 days.

(21) Appl. No.: 17/937,538

(22) Filed: Oct. 3, 2022

(65) Prior Publication Data

US 2023/0028375 A1      Jan. 26, 2023

Related U.S. Application Data

(63) Continuation of application No. PCT/US2021/025045, filed on Mar. 31, 2021.

(60) Provisional application No. 63/005,020, filed on Apr. 3, 2020.

(51) Int. Cl.
*A61F 2/24*          (2006.01)
*A61F 2/00*          (2006.01)

(52) U.S. Cl.
CPC .......... *A61F 2/2418* (2013.01); *A61F 2/0077* (2013.01); *A61F 2210/0076* (2013.01); *A61F 2250/001* (2013.01)

(58) Field of Classification Search
CPC .. A61F 2/24; A61F 2/2418; A61F 2210/0076; A61F 2/0077; A61F 2250/0069; A61F 2/2409; A61F 2/2412; A61F 2/2415; A61F 2/2439; A61F 2002/0086; A61F 2250/001; A61F 2240/001; A61F 2250/0015; D04B 21/00; D04B 1/00;
(Continued)

(56) References Cited

U.S. PATENT DOCUMENTS

| | | |
|---|---|---|
| 4,035,849 A | 7/1977 | Angell et al. |
| 5,411,552 A | 5/1995 | Andersen et al. |
| 5,554,185 A | 9/1996 | Block et al. |

(Continued)

FOREIGN PATENT DOCUMENTS

| | | | |
|---|---|---|---|
| CN | 104786564 A | 7/2015 | |
| CN | 109419573 A * | 3/2019 | ........... A61F 2/2418 |

(Continued)

*Primary Examiner* — Seema Mathew
(74) *Attorney, Agent, or Firm* — Klarquist Sparkman LLP

(57) ABSTRACT

A prosthetic heart valve including a frame, leaflet structure, and sealing member disposed around an outer surface of the frame is disclosed. As one example, the sealing member includes an inner layer and a plush outer layer comprising a plush outer surface. The inner layer is arranged against the outer surface of the frame and the outer layer is arranged against and attached to the inner layer. The inner layer is folded over at inflow and outflow ends, in an axial direction relative to a central longitudinal axis of the frame, to overlap respective ends of the outer layer and form tapered folds at opposite ends of the sealing member, each tapered fold including a narrower, first portion where the inner layer folds over and contacts itself and a wider, second portion where the inner layer overlaps an outer surface of an end portion of the outer layer.

23 Claims, 10 Drawing Sheets

(58) Field of Classification Search

CPC .... D04B 21/14; D04B 21/202; D03D 15/292;
D03D 15/30; D03D 15/41; D03D 15/47
See application file for complete search history.

(56) References Cited

U.S. PATENT DOCUMENTS

| | | | |
|---|---|---|---|
| 5,840,081 A | 11/1998 | Andersen et al. | |
| 6,168,614 B1 | 1/2001 | Andersen et al. | |
| 6,458,153 B1 | 10/2002 | Bailey et al. | |
| 6,582,462 B1 | 6/2003 | Andersen et al. | |
| 6,652,578 B2 | 11/2003 | Bailey et al. | |
| 6,689,162 B1 | 2/2004 | Thompson | |
| 7,018,408 B2 | 3/2006 | Bailey et al. | |
| 7,618,446 B2 | 11/2009 | Andersen et al. | |
| 7,785,366 B2 | 8/2010 | Maurer et al. | |
| 8,449,606 B2 | 5/2013 | Eliasen et al. | |
| 8,940,041 B2 | 1/2015 | Carlson et al. | |
| 8,945,209 B2 * | 2/2015 | Bonyuet | A61F 2/2415 623/2.18 |
| 9,283,072 B2 * | 3/2016 | Bruchman | A61F 2/2415 |
| 9,370,418 B2 * | 6/2016 | Pintor | A61F 2/2418 |
| 9,398,951 B2 * | 7/2016 | Alkhatib | A61F 2/2418 |
| 9,668,856 B2 * | 6/2017 | Para | A61F 2/2418 |
| 9,913,715 B2 * | 3/2018 | Braido | A61F 2/2418 |
| 10,179,043 B2 * | 1/2019 | Cohen-Tzemach | A61F 2/2418 |
| 10,232,564 B2 * | 3/2019 | Pelled | B29C 66/53245 |
| 10,413,401 B2 * | 9/2019 | Eberhardt | A61F 2/2409 |
| 11,096,781 B2 * | 8/2021 | Gurovich | A61F 2/2433 |
| 11,185,406 B2 * | 11/2021 | Haivatov | A61F 2/2409 |
| 11,839,559 B2 | 12/2023 | Shahriari | |
| 11,857,414 B2 * | 1/2024 | White | A61F 2/2427 |
| 12,064,341 B2 * | 8/2024 | Hoang | A61F 2/2418 |
| 12,279,949 B2 * | 4/2025 | Vidlund | A61F 2/2436 |
| 2004/0186589 A1 | 9/2004 | Bentele et al. | |
| 2004/0215320 A1 | 10/2004 | Machek | |
| 2005/0096736 A1 | 5/2005 | Osse et al. | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2006/0089672 A1 | 4/2006 | Martinek | |
| 2007/0037462 A1 | 2/2007 | Allen et al. | |
| 2007/0203575 A1 | 8/2007 | Forster et al. | |
| 2007/0265700 A1 | 11/2007 | Eliasen et al. | |
| 2008/0125853 A1 | 5/2008 | Bailey et al. | |
| 2010/0036484 A1 * | 2/2010 | Hariton | A61F 2/2433 623/2.18 |
| 2010/0174364 A1 * | 7/2010 | Hoffman | A61F 2/2418 623/2.17 |
| 2011/0224703 A1 | 9/2011 | Mortarino | |
| 2011/0282439 A1 * | 11/2011 | Thill | A61F 2/95 623/2.17 |
| 2012/0116492 A1 | 5/2012 | Seibold et al. | |
| 2013/0273795 A1 | 10/2013 | Richter | |
| 2013/0274873 A1 * | 10/2013 | Delaloye | A61F 2/2409 623/2.18 |
| 2013/0317526 A1 | 11/2013 | Mortarino | |
| 2014/0128964 A1 * | 5/2014 | Delaloye | A61F 2/2418 623/2.11 |
| 2014/0277528 A1 | 9/2014 | Mines et al. | |
| 2015/0005863 A1 * | 1/2015 | Para | A61F 2/2418 623/1.2 |
| 2015/0057685 A1 | 2/2015 | Serban et al. | |
| 2015/0073543 A1 * | 3/2015 | Thubrikar | A61F 2/2418 428/80 |
| 2015/0127088 A1 | 5/2015 | Carlson et al. | |
| 2015/0190552 A1 | 7/2015 | Richter | |
| 2015/0230953 A1 | 8/2015 | Bar et al. | |
| 2015/0320556 A1 * | 11/2015 | Levi | A61F 2/2412 29/515 |
| 2015/0327995 A1 * | 11/2015 | Morin | A61F 2/2418 623/2.17 |
| 2016/0029725 A1 | 2/2016 | Dee et al. | |
| 2017/0172736 A1 | 6/2017 | Chadha et al. | |
| 2018/0110617 A1 * | 4/2018 | Howard | A61F 2/2418 |
| 2018/0206982 A1 | 7/2018 | Haivatov et al. | |
| 2019/0038409 A1 * | 2/2019 | Schraut | A61F 2/2418 |
| 2019/0046314 A1 | 2/2019 | Levi et al. | |
| 2019/0076244 A1 | 3/2019 | Yohanan et al. | |
| 2019/0161892 A1 | 5/2019 | Kilickan et al. | |
| 2019/0192296 A1 | 6/2019 | Schwartz et al. | |
| 2019/0365530 A1 * | 12/2019 | Hoang | A61F 2/2409 |
| 2019/0374337 A1 | 12/2019 | Zamani et al. | |
| 2020/0188098 A1 | 6/2020 | Alkhatib et al. | |
| 2020/0306037 A1 * | 10/2020 | Siegel | A61M 25/0045 264/269 |
| 2022/0061984 A1 * | 3/2022 | Humair | A61F 2/2409 |
| 2022/0186410 A1 | 6/2022 | Sharma et al. | |
| 2022/0356614 A1 | 11/2022 | Zafiroglu et al. | |
| 2023/0017301 A1 | 1/2023 | Sherman et al. | |
| 2023/0103353 A1 | 4/2023 | Aders et al. | |
| 2023/0277287 A1 | 9/2023 | Greenhalgh et al. | |
| 2023/0277313 A1 * | 9/2023 | Gurovich | A61F 2/2433 623/2.18 |
| 2023/0397981 A1 | 12/2023 | Rocco et al. | |
| 2024/0000198 A1 * | 1/2024 | Sagara | D06C 13/08 |
| 2024/0041594 A1 * | 2/2024 | Eidenschink | A61F 2/2415 |
| 2024/0081982 A1 * | 3/2024 | Kibria | A61F 2/2415 |
| 2024/0180694 A1 * | 6/2024 | Loughnane | A61F 2/2418 |
| 2024/0307173 A1 * | 9/2024 | Ma | A61F 2/2433 |
| 2024/0382306 A1 * | 11/2024 | Nguyen-Thien-Nhon | A61F 2/2418 |
| 2025/0057646 A1 * | 2/2025 | Chen | A61F 2/2418 |
| 2025/0099232 A1 * | 3/2025 | Becerra | A61F 2/243 |
| 2025/0161034 A1 * | 5/2025 | Moore | A61F 2/2418 |
| 2025/0169946 A1 * | 5/2025 | King | A61F 2/2433 |

FOREIGN PATENT DOCUMENTS

| | | | | |
|---|---|---|---|---|
| CN | 111132634 B * | 5/2022 | | D03D 27/04 |
| DE | 19532846 A1 | 3/1997 | | |
| DE | 19907646 A1 | 8/2000 | | |
| EP | 0155245 A2 * | 9/1985 | | A61L 27/303 |
| EP | 0592410 B1 | 10/1995 | | |
| JP | 2011528256 A | 11/2011 | | |
| WO | 9117720 A1 | 11/1991 | | |
| WO | 0149213 A2 | 7/2001 | | |
| WO | 0247575 A2 | 6/2002 | | |
| WO | 2005084595 A1 | 9/2005 | | |
| WO | 2005102015 A2 | 11/2005 | | |
| WO | 2007067942 A1 | 6/2007 | | |
| WO | 2010121076 A2 | 10/2010 | | |
| WO | WO-2012048035 A2 * | 4/2012 | | A61F 2/2433 |
| WO | WO-2012178115 A2 * | 12/2012 | | A61F 2/2466 |
| WO | WO-2019144036 A1 * | 7/2019 | | A61F 2/2412 |
| WO | WO-2019175330 A1 * | 9/2019 | | A61F 2/07 |
| WO | WO-2021202636 A1 * | 10/2021 | | A61F 2/2433 |
| WO | WO-2022056048 A1 * | 3/2022 | | A61F 2/2418 |
| WO | WO-2022151891 A1 * | 7/2022 | | A61F 2/2433 |
| WO | WO-2025101859 A1 * | 5/2025 | | A61F 2/2433 |

* cited by examiner

MULTI-LAYER COVERING FOR A PROSTHETIC HEART VALVE

CROSS REFERENCE TO RELATED APPLICATION

This application is a continuation of PCT patent application no. PCT/US2021/025045 filed on Mar. 31, 2021, which application claims the benefit of U.S. Provisional Patent Application No. 63/005,020, filed Apr. 3, 2020, each of these applications being incorporated herein by reference in its entirety.

FIELD

The present disclosure relates to prosthetic heart valves, and in particular to prosthetic heart valves including a covering or sealing member.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Most expandable, transcatheter heart valves comprise a cylindrical metal frame or stent and prosthetic leaflets mounted inside the frame. These valves can also include one or more coverings (e.g., sealing members or skirts) spanning a circumference of the frame, on an inner or outer surface of the frame. These coverings can be configured to establish a seal with the native tissue when the prosthetic valve is placed at the implantation site (and thus may be referred to as sealing members). In some embodiments, a single-layered, woven cloth skirt alone may not provide sufficient sealing against the native annulus of the heart. In other embodiments, the valve may include both an inner skirt (on an inside of the frame) and an outer skirt (on an outside of the frame). However, such skirt arrangements may result in a bulkier valve with a larger crimp profile.

Accordingly, a need exists for improved prosthetic heart valve coverings.

SUMMARY

Described herein are embodiments of coverings for a prosthetic heart valve and methods of making and using such coverings. The prosthetic heart valve can include a frame and a leaflet assembly arranged on an inner surface of the frame. The prosthetic heart valve can include a covering, in the form of a sealing member, arranged around a circumference of the frame and on an outer surface of the frame. The sealing member can include a woven inner layer and a knitted outer layer, the knitted outer layer configured to promote tissue growth and seal against native tissue when the valve is implanted and the woven inner layer configured to reduce tissue growth and protect leaflets of the leaflet assembly from abrasion from the inner layer. As such, end portions of the inner layer can overlap end portions of the outer layer, forming tapered folds at either end of the sealing member.

In one representative embodiment, a prosthetic heart valve includes: a frame comprising a plurality of struts, the frame being radially collapsible and expandable between a collapsed configuration and an expanded configuration, the frame having an inflow end and an outflow end; at leaflet structure situated at least partially within the frame; and a sealing member disposed around an outer surface of the frame. The sealing member includes: an inner layer comprising a woven fabric; and an outer layer comprising a knitted fabric. The knitted fabric comprises a base layer including a plurality of courses formed from a first base yarn and a second base yarn that are knit together and a plurality of wales formed from a warp yarn, where each loop of the warp yarn is knit together with the first base yarn and second base yarn of two adjacent courses. The inner layer is arranged against the outer surface of the frame and the outer layer is arranged against and attached to the inner layer and the inner layer is folded over at either end, in an axial direction relative to a central longitudinal axis of the frame, to form folds that overlap respective ends of the outer layer.

In another representative embodiment, a prosthetic heart valve includes: a frame comprising a plurality of struts, the frame being radially collapsible and expandable between a collapsed configuration and an expanded configuration, the frame having an inflow end and an outflow end; at leaflet structure situated at least partially within the frame; and a sealing member disposed around an outer surface of the frame, the sealing member extending in an axial direction from the inflow end to a mid-point of the frame, the axial direction relative to a central longitudinal axis of the frame, the mid-point arranged between the inflow end and outflow end. The sealing member includes: an inner layer comprising a woven fabric; and an outer layer comprising a knitted fabric, the knitted fabric comprising a base layer formed from a first base yarn and a second base yarn that are knit together and a plush outer surface formed from a plurality of pile yarns that are knit into loops and that extend outward from the base layer. The inner layer is arranged against the outer surface of the frame and the outer layer is arranged against and attached to the inner layer and wherein the inner layer is folded over at both ends of the sealing member, the ends arranged opposite one another along the axial direction, to form folds that overlap respective ends of the outer layer.

In yet another representative embodiment, a prosthetic heart valve includes: a frame comprising a plurality of struts, the frame being radially collapsible and expandable between a collapsed configuration and an expanded configuration, the frame having an inflow end and an outflow end; at leaflet structure situated at least partially within the frame; and a sealing member disposed around an outer surface of the frame, the sealing member extending in an axial direction from the inflow end to a mid-point of the frame, the axial direction relative to a central longitudinal axis of the frame, the mid-point arranged between the inflow end and outflow end. The sealing member includes: an inner layer comprising a woven fabric; and an outer layer comprising a knitted fabric. The knitted fabric includes: a base layer including a plurality of courses formed from a first base yarn and a second base yarn that are knit together and a plurality of wales formed from a warp yarn, where each loop of the warp yarn is knit together with the first base yarn and second base yarn of two adjacent courses; and a plush outer surface formed from a plurality of pile yarns that are knit into loops and that extend outward from the base layer. The inner layer is arranged against the outer surface of the frame and the outer layer is arranged against and attached to the inner layer and the inner layer is folded over at either end of the sealing member to form tapered folds, each tapered fold overlapping a respective end of the outer layer at a wider portion of the tapered fold.

The foregoing and other objects, features, and advantages of the disclosed technology will become more apparent from the following detailed description, which proceeds with reference to the accompanying figures.

DETAILED DESCRIPTION

General Considerations

Figures 1, 2A, 2B:
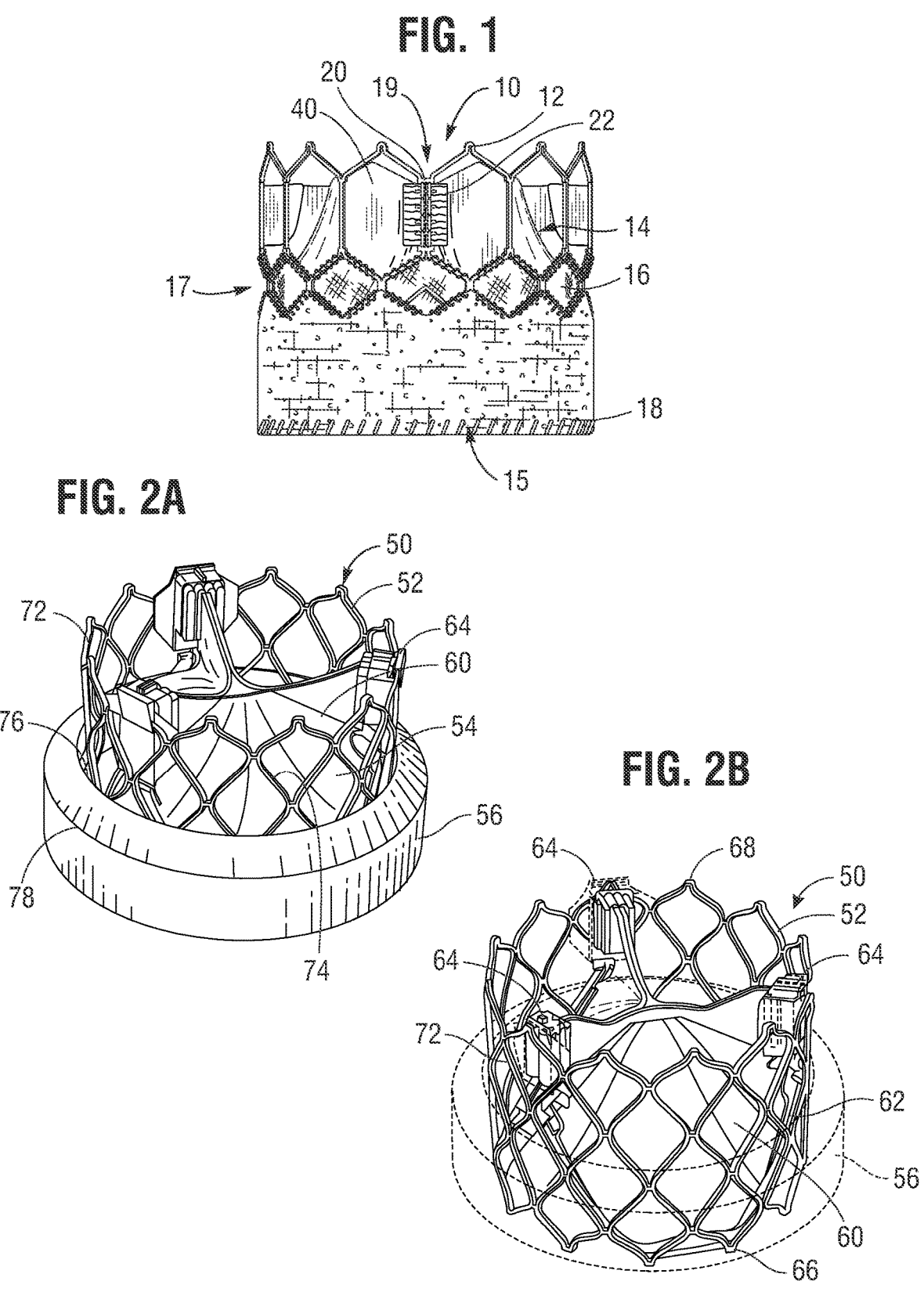
FIG. 1 is a perspective view of a prosthetic heart valve, according to one embodiment.
FIG. 2A is a perspective view of a prosthetic heart valve, according to another embodiment.
FIG. 2B is a perspective view of the prosthetic valve of FIG. 2A with the components on the outside of the frame shown in transparent lines for purpose of illustration.

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

As used herein, with reference to the prosthetic heart valve and the delivery apparatus, "proximal" refers to a position, direction, or portion of a component that is closer to the user and/or a handle of the delivery apparatus that is outside the patient, while "distal" refers to a position, direction, or portion of a component that is further away from the user and/or the handle of the delivery apparatus and closer to the implantation site. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the longitudinal axis of the prosthetic valve).

Examples of the Disclosed Technology

Described herein are examples of prosthetic heart valves, coverings or sealing members for prosthetic heart valves, and methods of making coverings or sealing members for prosthetic heart valves. The prosthetic heart valves may include a frame, a leaflet assembly including a plurality of leaflets arranged on and attached to an inner surface of the frame, and a sealing member arranged on and around an outer surface of the frame.

In some embodiments, the sealing member can comprise a woven inner layer and a knitted outer layer. The sealing member can include an upper (or outflow) fold formed by an upper end portion (outflow end portion) of the inner layer folded over itself and extending inward to overlap an upper end portion (outflow end portion) of the outer layer and a lower (or inflow) fold formed by a lower end portion (inflow end portion) of the inner layer folded over itself and extending inward to overlap a lower end portion (inflow end portion) of the outer layer. The upper fold can be arranged at a mid-point of the frame and the lower fold can be arranged at an inflow end of the frame. The upper and lower folds (which can also be referred to herein as first and second folds) create a taper at either end of the sealing member, thereby reducing an overall crimp profile of the valve and reducing push forces during delivery of the valve, crimped onto a delivery device, through an introducer sheath and to a target implantation site.

The outer layer can be configured to promote tissue growth and seal with native tissue of an annulus of a heart (e.g., after implantation of the valve). The inner layer can be configured to decrease tissue growth and block the leaflets from contacting an inner or back surface of the outer layer, thereby reducing potential abrasion to the leaflets.

Embodiments of the disclosed technology, including the disclosed sealing members or skirts, can be used in combination with various prosthetic heart valves configured for implantation at various locations within the heart.

FIG. 1 shows a prosthetic heart valve 10, according to one embodiment. Any of the prosthetic valves disclosed herein are adapted to be implanted in the native aortic annulus, although in other embodiments they can be adapted to be implanted in the other native annuluses of the heart (e.g., the pulmonary, mitral, and tricuspid valves). The disclosed prosthetic valves also can be implanted within vessels communicating with the heart, including a pulmonary artery (for replacing the function of a diseased pulmonary valve, or the superior vena cava or the inferior vena cava (for replacing the function of a diseased tricuspid valve).

The prosthetic valve 10 can have four main components: a stent or frame 12, a valvular structure 14, an inner skirt 16, and a perivalvular outer sealing member or outer skirt 18. The prosthetic valve 10 can have an inflow end portion 15, an intermediate portion 17, and an outflow end portion 19. The inner skirt 16 can be arranged on and/or coupled to an inner surface of the frame 12 while the outer skirt 18 can be arranged on and/or coupled to an outer surface of the frame 12.

The valvular structure 14 can comprise three leaflets 40, collectively forming a leaflet structure, which can be arranged to collapse in a tricuspid arrangement, although in other embodiments there can be greater or fewer number of leaflets (e.g., one or more leaflets 40). The leaflets 40 can be secured to one another at their adjacent sides to form commissures 22 of the leaflet structure 14. The lower edge of valvular structure 14 can have an undulating, curved scalloped shape and can be secured to the inner skirt 16 by sutures (not shown). In some embodiments, the leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The frame 12 can be formed with a plurality of circumferentially spaced slots, or commissure windows 20 that are adapted to mount the commissures 22 of the valvular structure 14 to the frame. The frame 12 can be made of any of various suitable plastically-expandable materials (e.g., stainless steel, etc.) or g-expanding materials (e.g., nickel titanium alloy (NiTi), such as nitinol), as known in the art. In some embodiments, when constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pennsylvania), which is equivalent to UNS R30035 alloy (covered by ASTM F562-02). MP35N® alloy/UNS R30035 alloy comprises 35% nickel, 35% cobalt, 20% chromium, and 10% molybdenum, by weight. Additional details regarding the prosthetic valve 10 and its various components are described in WIPO Patent Application Publication No. WO 2018/222799, which is incorporated herein by reference.

FIG. 2A is a perspective view of a prosthetic heart valve 50, according to another embodiment. The valve 50 can have three main components: a stent or frame, 52, a valvular structure 54, and a sealing member 56. FIG. 2B is a perspective view of the prosthetic valve 50 with the components on the outside of the frame 52 (including the sealing member 56) shown in transparent lines for purposes of illustration.

Like the valvular structure 14 of FIG. 1, the valvular structure 54 can comprise three leaflets 60, collectively forming a leaflet structure, which can be arranged to collapse in a tricuspid arrangement. Each leaflet 60 can be coupled to the frame 52 along its inflow edge 62 (the lower edge in the figures; also referred to as "cusp edges") and at commissures 64 of the valvular structure 54 where adjacent portions of two leaflets are connected to each other. A reinforcing element (not shown), such as a fabric strip, can be connected directly to the cusp edges of the leaflets and to the struts of the frame to couple the cusp edges of the leaflets to the frame.

Similar to the frame 12 of FIG. 1, the frame 52 can be made of any of various suitable plastically-expandable materials or self-expanding materials, as known in the art and described above. The frame 52 in the illustrated embodiment comprises a plurality of circumferentially extending rows of angled struts 72 defining rows of cells, or openings, 74 of the frame. The frame 52 can have a cylindrical or substantially cylindrical shape having a constant diameter from an inflow end 66 to an outflow end 68 of the frame as shown, or the frame can vary in diameter along the height of the frame, as disclosed in U.S. Patent Publication No. 2012/0239142, which is incorporated herein by reference.

The sealing member 56 in the illustrated embodiment is mounted on the outside of the frame 52 and functions to create a seal against the surrounding tissue (e.g., the native leaflets and/or native annulus) to prevent or at least minimize paravalvular leakage. The sealing member 56 can comprise an inner layer 76 (which can be in contact with the outer surface of the frame 52) and an outer layer 78. The sealing member 56 can be connected to the frame 52 using suitable techniques or mechanisms. For example, the sealing member 56 can be sutured to the frame 52 via sutures that can extend around the struts 72 and through the inner layer 76. In alternative embodiments, the inner layer 76 can be mounted on the inner surface of the frame 52, while the outer layer 78 is on the outside of the frame 52.

The outer layer 78 can be configured or shaped to extend radially outward from the inner layer 76 and the frame 52 when the prosthetic valve 50 is deployed. When the prosthetic valve is fully expanded outside of a patient's body, the outer layer 78 can expand away from the inner layer 76 to create a space between the two layers. Thus, when implanted inside the body, this allows the outer layer 78 to expand into contact with the surrounding tissue, such as a native annulus.

Additional details regarding the prosthetic valve 50 and its various components are described in U.S. Patent Publication No. 2018/0028310, which is incorporated herein by reference.

Figure 16:
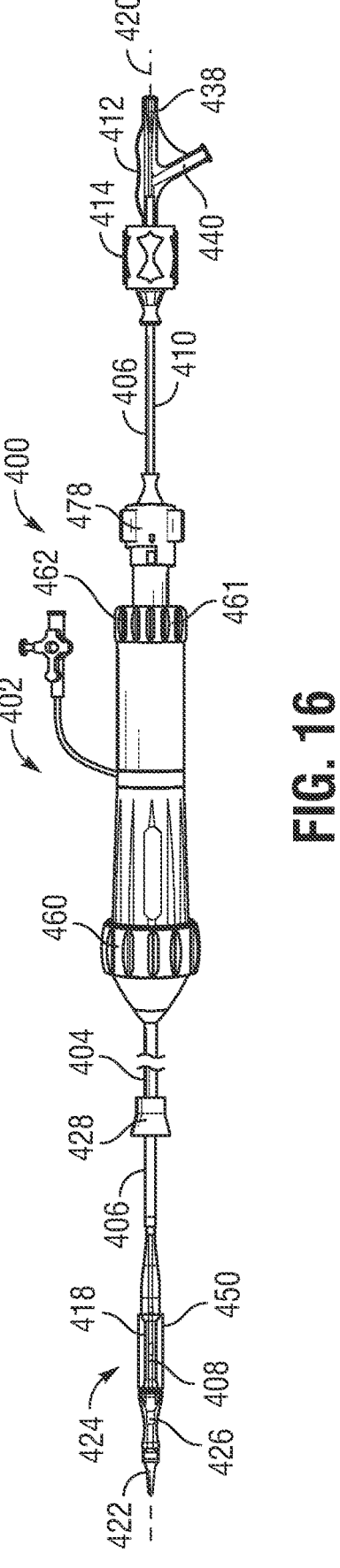
FIG. 16 is a side view of an embodiment of a delivery apparatus configured to deliver and implant a radially expandable prosthetic heart valve at an implantation site.

FIG. 16 shows a delivery apparatus 400, according to an embodiment, that can be used to implant an expandable prosthetic heart valve (e.g., prosthetic heart valve 10 of FIG. 1, prosthetic heart valve 50 of FIGS. 2A-2B, or any of the other prosthetic heart valves described herein). In some embodiments, the delivery apparatus 400 is specifically adapted for use in introducing a prosthetic valve into a heart.

The delivery apparatus 400 in the illustrated embodiment of FIG. 16 is a balloon catheter comprising a handle 402 and a steerable, outer shaft 404 extending distally from the handle 402. The delivery apparatus 400 can further comprise an intermediate shaft 406 (which also may be referred to as a balloon shaft) that extends proximally from the handle 402 and distally from the handle 402, the portion extending distally from the handle 402 also extending coaxially through the outer shaft 404. Additionally, the delivery apparatus 400 can further comprise an inner shaft 408 extending distally from the handle 402 coaxially through the intermediate shaft 406 and the outer shaft 404 and proximally from the handle 402 coaxially through the intermediate shaft 406.

The outer shaft 404 and the intermediate shaft 406 can be configured to translate (e.g., move) longitudinally, along a central longitudinal axis 420 of the delivery apparatus 400, relative to one another to facilitate delivery and positioning of a prosthetic valve at an implantation site in a patient's body.

The intermediate shaft 406 can include a proximal end portion 410 that extends proximally from a proximal end of the handle 402, to an adaptor 412. A rotatable knob 414 can be mounted on the proximal end portion 410 and can be configured to rotate the intermediate shaft 406 around the central longitudinal axis 420 and relative to the outer shaft 404.

The adaptor 412 can include a first port 438 configured to receive a guidewire therethrough and a second port 440 configured to receive fluid (e.g., inflation fluid) from a fluid source. The second port 440 can be fluidly coupled to an inner lumen of the intermediate shaft 406.

The intermediate shaft 406 can further include a distal end portion that extends distally beyond a distal end of the outer shaft 404 when a distal end of the outer shaft 404 is positioned away from an inflatable balloon 418 of the delivery apparatus 400. A distal end portion of the inner shaft 408 can extend distally beyond the distal end portion of the intermediate shaft 406.

The balloon 418 can be coupled to the distal end portion of the intermediate shaft 406.

In some embodiments, a distal end of the balloon 418 can be coupled to a distal end of the delivery apparatus 400, such as to a nose cone 422 (as shown in FIG. 16), or to an alternate component at the distal end of the delivery apparatus 400 (e.g., a distal shoulder). An intermediate portion of the balloon 418 can overlay a valve mounting portion 424 of a distal end portion of the delivery apparatus 400 and a distal end portion of the balloon 418 can overlay a distal shoulder 426 of the delivery apparatus 400. The valve mounting portion 424 and the intermediate portion of the balloon 418 can be configured to receive a prosthetic heart valve in a radially compressed state. For example, as shown schematically in FIG. 16, a prosthetic heart valve 450 (which can be one of the prosthetic valves described herein) can be mounted around the balloon 418, at the valve mounting portion 424 of the delivery apparatus 400.

The balloon shoulder assembly, including the distal shoulder 426, is configured to maintain the prosthetic heart valve 450 (or other medical device) at a fixed position on the balloon 418 during delivery through the patient's vasculature.

The outer shaft 404 can include a distal tip portion 428 mounted on its distal end. The outer shaft 404 and the intermediate shaft 406 can be translated axially relative to one another to position the distal tip portion 428 adjacent to a proximal end of the valve mounting portion 424, when the prosthetic valve 450 is mounted in the radially compressed state on the valve mounting portion 424 (as shown in FIG. 16) and during delivery of the prosthetic valve to the target implantation site. As such, the distal tip portion 428 can be configured to resist movement of the prosthetic valve 450 relative to the balloon 418 proximally, in the axial direction, relative to the balloon 418, when the distal tip portion 428 is arranged adjacent to a proximal side of the valve mounting portion 424.

An annular space can be defined between an outer surface of the inner shaft 408 and an inner surface of the intermediate shaft 406 and can be configured to receive fluid from a fluid source via the second port 440 of the adaptor 412. The annular space can be fluidly coupled to a fluid passageway formed between the outer surface of the distal end portion of the inner shaft 408 and an inner surface of the balloon 418. As such, fluid from the fluid source can flow to the fluid passageway from the annular space to inflate the balloon 418 and radially expand and deploy the prosthetic valve 450.

An inner lumen of the inner shaft can be configured to receive a guidewire therethrough, for navigating the distal end portion of the delivery apparatus 400 to the target implantation site.

The handle 402 can include a steering mechanism configured to adjust the curvature of the distal end portion of the delivery apparatus 400. In the illustrated embodiment, for example, the handle 402 includes an adjustment member, such as the illustrated rotatable knob 460, which in turn is operatively coupled to the proximal end portion of a pull wire. The pull wire can extend distally from the handle 402 through the outer shaft 404 and has a distal end portion affixed to the outer shaft 404 at or near the distal end of the outer shaft 404. Rotating the knob 460 can increase or decrease the tension in the pull wire, thereby adjusting the curvature of the distal end portion of the delivery apparatus 400. Further details on steering or flex mechanisms for the delivery apparatus can be found in U.S. Pat. No. 9,339,384, which is incorporated by reference herein.

The handle 402 can further include an adjustment mechanism 461 including an adjustment member, such as the illustrated rotatable knob 462, and an associated locking mechanism including another adjustment member, configured as a rotatable knob 478. The adjustment mechanism 461 is configured to adjust the axial position of the intermediate shaft 406 relative to the outer shaft 404 (e.g., for fine positioning at the implantation site). Further details on the delivery apparatus 400 can be found in U.S. Provisional Application Nos. 63/069,567 and 63/138,890, which are incorporated by reference herein.

In some embodiments, prosthetic heart valves can include a single-layer sealing member or outer skirt that comprises a woven material. However, this type of skirt can be expensive to manufacture and not seal well against the tissue of a native annulus of the heart. In some embodiments, a two-layer sealing member or outer skirt comprising different materials or differently constructed materials (e.g., a same material with different cloth or fabric construction) may help to address some of these issues, such as improving sealing against the native tissue while reducing costs. However, two-layer skirts may be bulky and increase pushing forces through an introducer of a valve delivery system, thereby increasing a difficulty in delivering a compressed valve to a target implantation site in the heart. Further, outer layers of two-layer skirts may cause abrasion against the leaflets of the valve, which may decrease their longevity.

Figure 3:
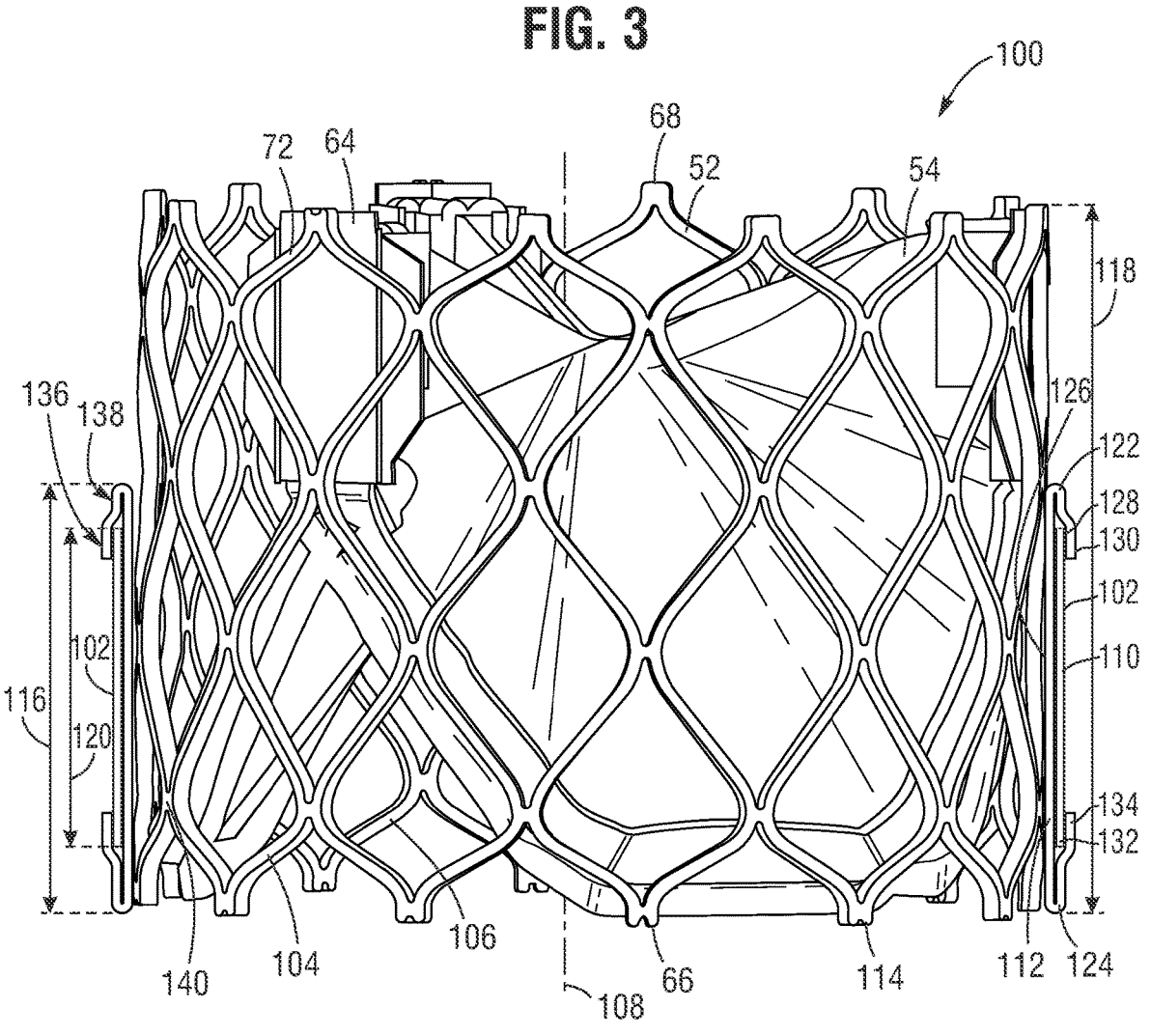
FIG. 3 is a cross-sectional, side view of a multi-layer skirt arranged around a circumference of an outer surface of a frame of an exemplary prosthetic heart valve.
Figure 4:
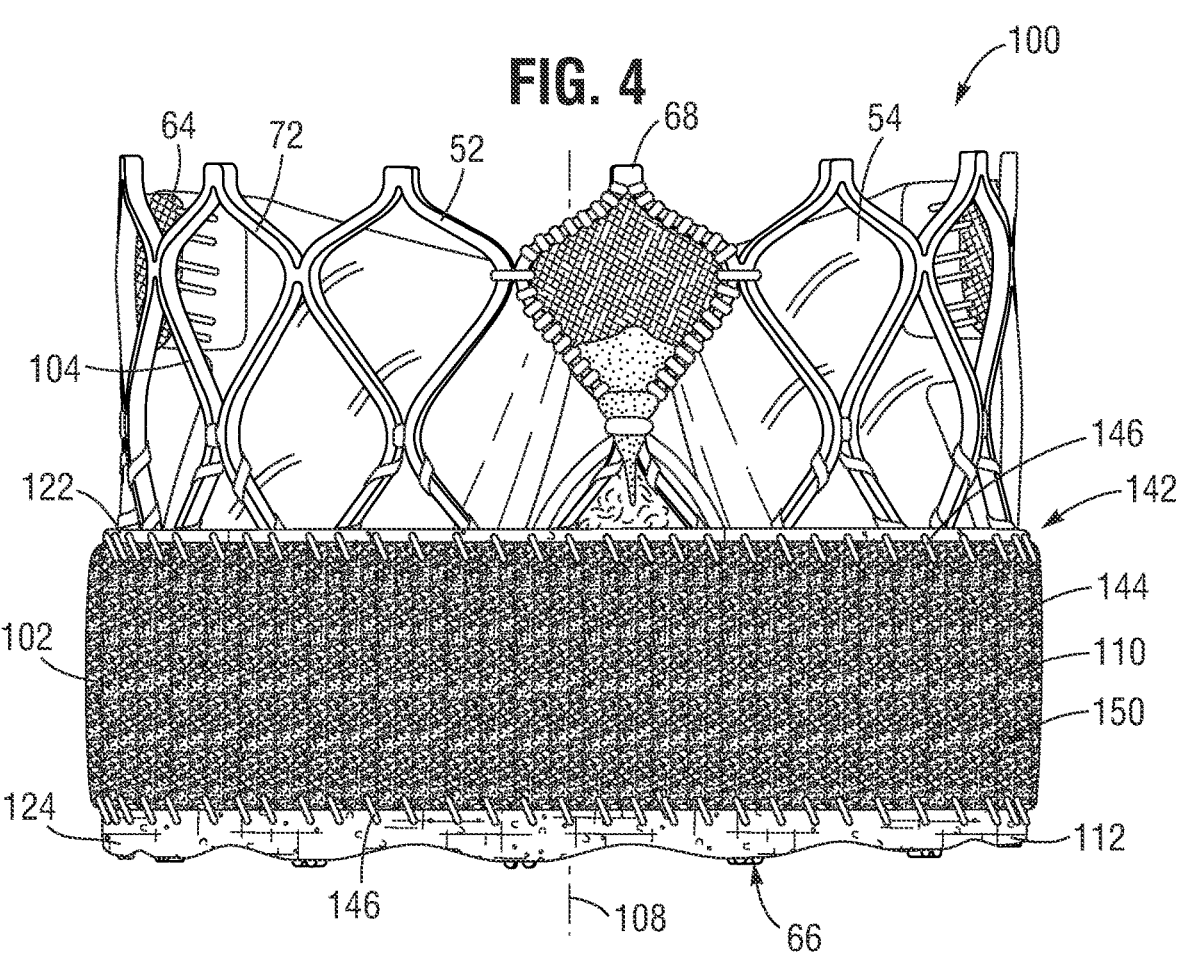
FIG. 4 is a side view of the multi-layer skirt arranged around the circumference of the outer surface of the frame of the exemplary prosthetic heart valve of FIG. 3.
Figure 5:
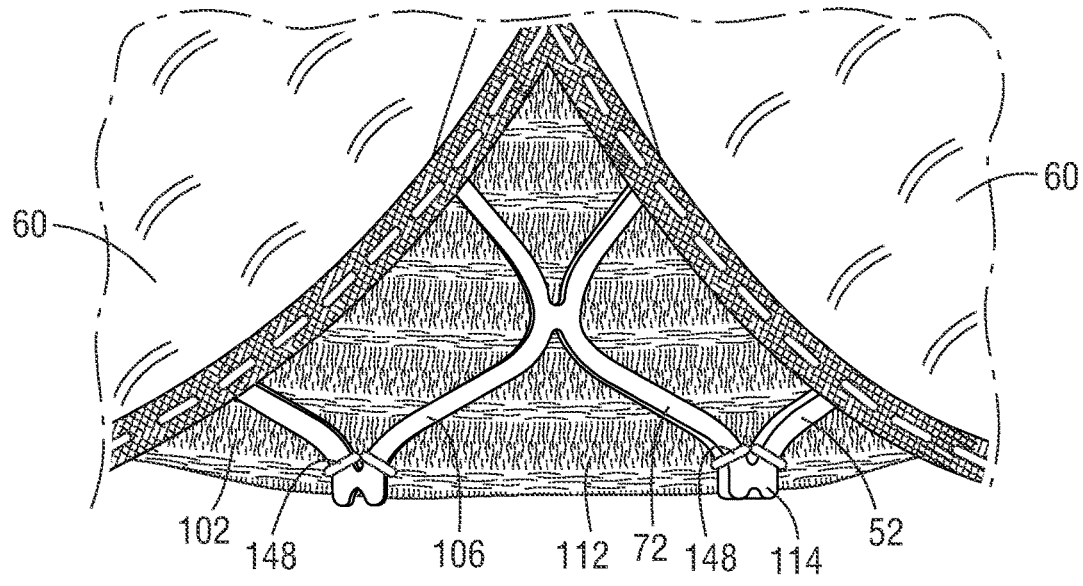
FIG. 5 is a detail view of a portion of an inner surface of the frame and the multi-layer skirt of the exemplary prosthetic heart valve of FIG. 3.
Figure 15:
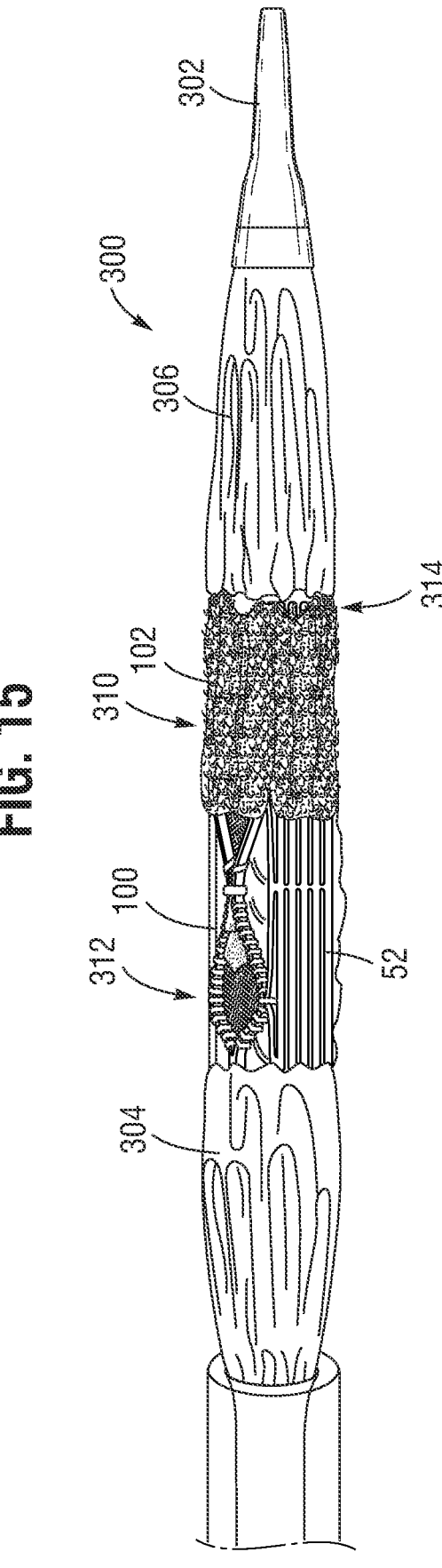
FIG. 15 is a side view of the prosthetic heart valve including the multi-layer skirt of FIG. 4, crimped onto a delivery device.

FIGS. 3-15 show an embodiment of a two-layer skirt (e.g., sealing member or covering) 102 for a prosthetic heart valve that is configured to promote tissue growth and provide increased sealing against tissue of a native annulus of the heart while also protecting the leaflets of the prosthetic heart valve and reducing push forces experienced during delivery of the valve to the target implantation site in the heart. For example, FIG. 3 shows a cross-sectional, side view of the skirt 102 on an exemplary prosthetic heart valve. FIGS. 4 and 5 show an outer view and inner view, respectively, of the skirt 102 on the exemplary prosthetic heart valve. FIGS. 6-11 show different views or portions of the skirt 102, highlighting the specific cloth construction of the two layers of the skirt 102. FIGS. 12-14 show the skirt 102 on the exemplary prosthetic heart valve in different stages of deployment (e.g., during implantation at the target implantation site), while FIG. 15 shows the skirt 102 on the exemplary prosthetic heart valve, where the valve is in a crimped state on a delivery device.

It should be noted that while the skirt 102 is shown on the valve 100 including the frame 52 and the valvular structure 54 in FIGS. 3-5 and 12-15, as described further below, in alternate embodiments, the skirt 102 may be arranged on an outer surface of a different type of frame of a different prosthetic heart valve. For example, in some embodiments, the skirt 102 may replace the outer skirt 18 of prosthetic heart valve 10 of FIG. 1.

Turning first to FIG. 3, a side view of a prosthetic heart valve 100, according to an embodiment, is shown. The valve 100 includes the frame 52 and valvular structure 54 of the valve 50 shown in FIGS. 2A and 2B. However, the valve 100 includes a different outer sealing member (also referred to herein as an "outer covering" or "skirt") 102 from that of the valve 50. The skirt 102 is shown in cross-section in FIG. 3 to illustrate its different layers.

The skirt 102 is arranged on an outer surface 104 of the frame 52, where the outer surface 104 is arranged opposite an inner surface 106 of the frame 52, the inner and outer surfaces relative to a radial direction that is relative to a central longitudinal axis 108 of the valve 100. As shown in FIG. 3, the commissures 64 are attached to the inner surface 106 while the outer skirt 102 is arranged on the outer surface, around an entire circumference of the frame 52 (e.g., as shown in FIG. 4, as described further below).

As introduced above and shown in FIG. 3, the skirt 102 is a two-layer skirt 102 including an outer layer 110 and an inner layer 112 which are coupled to one another. In some embodiments, the outer layer 110 can comprise a knitted, woven, braided, or non-woven material, which may result in a softer, plush (e.g., fuzzy) surface in appearance and/or texture. In some embodiments, the inner layer 112 can comprise a woven material. The outer layer 110 may be configured to promote tissue growth for sealing of the valve 100 against the native tissue (e.g., when implanted), while the inner layer may be configured to reduce tissue growth and protect the leaflets of the valvular structure 54 from abrasions from the outer layer 110. Further details on the material construction of the outer layer 110 and inner layer 112 of the skirt 102 are discussed below with reference to FIGS. 4-11.

As shown in FIG. 3, an inner (e.g., radially inward-facing) surface of the inner layer 112 is arranged adjacent to and positioned against the outer surface 104 of the struts of the frame 52, along and around an entire circumference of the frame 52 (as shown in FIG. 4, for example). Further, the outer layer 110 is disposed on (e.g., positioned against) the inner layer 112. More specifically, an inner (e.g., radially inward-facing) surface of the outer layer 110 is in face-sharing contact with an outer (e.g., radially outward-facing) surface of the inner layer 112.

In some embodiments, as shown in FIG. 3, the skirt 102 extends, in an axial direction relative to the central longitudinal axis 108, from inflow apices 114 of the frame 52 (e.g., apices arranged at the inflow end 66) to a location approximately mid-way between the outflow end 68 and the inflow end 66 of the frame 52 (e.g., approximately mid-frame). In some embodiments, the skirt 102 can extend to a mid-point of the frame, in the axial direction, that is equidistant between the outflow end 68 and the inflow end 66. In other embodiments, the skirt 102 can extend to a mid-point of the frame, in the axial direction, that is arranged between the outflow end 68 and the inflow end 66, but closer to the inflow end 66 than the outflow end 68. In still other embodiments, the skirt 102 can extend to a mid-point of the frame, in the axial direction, that is arranged between the outflow end 68 and the inflow end 66, but closer to the outflow end 68 than the inflow end 66. In other embodiments, the skirt 102 can extend the entire height or substantially the entire of the frame from the inflow end 66 to the outflow end 68. In other embodiments, the skirt 102 can extend from the outflow end 68 to a location offset and downstream of the inflow end 66. In still other embodiments, the skirt 102 can be offset upstream from the outflow end 68 and offset downstream from the inflow end 66.

As shown in FIG. 3, the inner layer 112 can have a length 116 (arranged in the axial direction) that is shorter than a length 118 of the frame 52 and longer than a length 120 of the outer layer 110. While the inner layer 112 can extend from the inflow apices 114 to the mid-point of the frame 52, the outer layer 110 can extend from a first point that is a distance away (e.g., inward along the axial direction) from the inflow apices 114 to a second point that is a distance away from (e.g., short of) the mid-point of the frame 52. In some embodiments, the first point may be at or proximate to a first rung 140 of the frame 52.

By having the inner layer 112 and the outer layer 110 of the skirt have different lengths, as explained above, the overall crimp profile of the valve 100 may be reduced (e.g., as shown in FIG. 15). Further, by having the outer layer 110 not extend all the way to the inflow end 66 of the frame (e.g., to the inflow apices), the crimp profile at the bulkier, inflow end 66 of the valve 100 may be reduced. While the length 120 of the outer layer 110 is reduced relative to the length 116 of the inner layer 112, the length 120 of the outer layer 110 can still be selected to provide the largest possible surface area for contact with the native tissue, once implanted.

In some embodiments the length 116 of the inner layer 112 can be in a range of 13-17 mm and the length 120 of the outer layer 110 can be in a range of 7.0-15 mm. In other embodiments, the length 116 of the inner layer 112 can be in a range of 13-17 mm and the length 120 of the outer layer 110 can be in a range of 7-13 mm.

The length 116 of the inner layer 112 may be an effective, folded length of the inner layer 112 when assembled on the frame (e.g., as shown on the valve in FIG. 3). However, the unfolded, manufactured length of the inner layer (length 117 shown in FIG. 6) is longer, in order to accommodate the folds over the ends of the outer layer 110. For example, as shown in FIG. 3, the skirt 102 includes an upper, first fold 122 arranged at the end of the skirt 102 located closest to the outflow end 68 of the frame 52 and a lower, second fold 124 arranged at the end of the skirt 102 located closest to the inflow end 66 of the frame 52. Said another way, the second fold 124 is arranged at (e.g., proximate to) the inflow apices 114 of the frame 52 and the first fold 122 is arranged further away from the inflow apices 114 (than the second fold 124).

Each of the first fold 122 and the second fold 124 are formed by a different (opposite) ends of the inner layer 112. For example, the first fold 122 is formed by folding an upper or outflow, first end of the inner layer 112 over from an axially-extending, main portion 126 of the inner layer 112, at a location arranged outward, in the axial direction, from an upper or outflow, first end portion 128 of the outer layer 110 (e.g., the end arranged closer to the outflow end 68), and over the first end portion 128 of the outer layer 110. As a result, a first end portion 130 of the inner layer 112 overlaps the outer surface of the first end portion 128 of the outer layer 110.

Similarly, the second fold 124 is formed by folding a lower or inflow, second end of the inner layer 112 over from the axially-extending, main portion 126 of the inner layer 112, at a location arranged outward, in the axial direction, from a lower or inflow, second end portion 132 of the outer layer 110 (e.g., the end arranged closer to the inflow end 66), and over the second end portion 132 of the outer layer 110. As a result, a second end portion 134 of the inner layer 112 overlaps the outer surface of the second end portion 132 of the outer layer 110.

As shown in FIG. 3, each of the first fold 122 and the second fold 124 creates a taper (e.g., narrower portion) at either end of the skirt 102. For example, each axial end of the skirt 102 has a wider portion 136 formed by overlapping layers of the inner layer 112 and the outer layer 110 (e.g., three overlapping layers in total) and a narrower portion 138 formed by two overlapping layers of the inner layer 112. The narrower portion 138 is arranged outward, in the axial direction, from the wider portion 136. As a result, the ends of the skirt 102 each taper (e.g., narrow) from the respective end of the outer layer 110 to the respective end of the skirt 102.

The first fold 122 may help to cover, and therefore protect, the leaflets from the fuzzy or plush edges of the outer layer 110, thereby reducing abrasion to the leaflets. The second fold 124 may help to reduce push forces when inserting the prosthetic heart valve, crimped onto a delivery device (e.g., as shown in FIG. 15), into and through an introducer sheath, when advancing the valve to the target implantation site.

For example, as shown in FIG. 15, the valve 100, including the frame 52 and the skirt 102, can be crimped onto a delivery device 300. In some embodiments, as shown in FIG. 15, the valve 100 can be crimped onto the delivery device 300, inward of (proximal to) a nosecone 302 and between a proximal shoulder (disposed inside a proximal section 304 of an inflatable balloon of the delivery device 300) and distal shoulder (disposed inside a distal section 306 of the inflatable balloon) of the delivery device 300. As shown in FIG. 15, the overall crimp profile of the valve 100 may be reduced (e.g., as compared to other valves having multi-layer skirts) due to the construction of the inner and outer layers of the skirt 102, as described herein (e.g., a crimped diameter of a skirt portion 310 of the valve 100 including the skirt 102 may only be slightly larger than a crimped diameter of a frame portion 312 of the valve 100 that does not include the skirt 102). Further, the tapering of the lower fold 124, arranged at the distal end 314 of the skirt (e.g., inflow end of valve 100), the distal end 314 arranged closest to the nosecone 302, may help to reduce push forces when advancing the valve 100, on the delivery device 300, into and through an introducer coupled with an introducer sheath inserted in a patient's vasculature.

FIG. 4 shows an outer view (e.g., from outside the valve 100) of the skirt 102 attached to and extending around a circumference of the outer surface 104 of the valve 100. As explained above with reference to FIG. 3 and is also shown in FIG. 4, the skirt 102 extends, in the axial direction, from the inflow end 66 of the valve 100 to a mid-point 142 of the valve 100.

An exposed, outer surface 144 of the outer layer 110 is shown in FIG. 4, with the upper, first fold 122 and lower, second fold 124 extending above and below, respectively, the exposed, outer surface. In some embodiments, as shown in FIG. 4, the lower, second fold 124 may be longer, in the axial direction, than the upper, first fold 122. As explained above, this configuration may help to reduce the crimp profile and overall bulkiness of the valve 100 at the inflow end 66.

In some embodiments, as shown in FIG. 4, the inner layer 112 and the outer layer 110 of the skirt 102 are connected (e.g., coupled) together, at their folded over, overlapping regions (e.g., proximate to folds 122 and 124), via a plurality of whip stitches 146. More specifically, the whip stitches 146 can be made in the taper of each of the folds 122 and 124 to allow for stretching between the valve's crimped and expanded configurations (e.g., as shown in FIGS. 12-14, as described further below). For example, a first line of whip stitches 146 is arranged at the first fold 122, around the entire circumference of the frame 52, and a second line of whip stitches 146 is arranged at the second fold 124, around the entire circumference of the frame 52.

As an example, FIGS. 12-14 show the valve 100 in three expanded (e.g., expanded relative to a compressed or crimped configuration, as shown in FIG. 15) configurations, including a first expanded configuration 200 (FIG. 12), a second expanded configuration 202 (FIG. 13), and a third expanded configuration 204 (FIG. 14). The first expanded configuration 200 shown in FIG. 12 shows the valve 100 in an exemplary, as built, expanded size (e.g., expanded to its target diameter). The second expanded configuration 202 shown in FIG. 13 shows the valve 100 in an under deployed state (e.g., expanded to a diameter that is smaller than its as built, or target diameter). In contrast, the third expanded configuration 204 shown in FIG. 14 shows the valve 100 in an over deployed state (e.g., expanded to a diameter that is larger than its as built, or target diameter).

Each of FIGS. 12-14 shows a varying degree of a scallop-like (e.g., undulating or wave-like) shape to an inflow edge 206 of the skirt 102. The scallop or wave-like shape of the inflow edge 206 can be created by the inflow edge 206 being arranged at and/or attached to each inflow apex 114 of the frame 52 and then undulating inward, away from the inflow end 66 and toward the outflow end 68, of the frame 52, creating an inward crest (e.g., peak) 208 in the scalloped inflow edge 206 between each set of adjacent inflow apices 114.

For example, in the second expanded configuration (e.g., the under deployed configuration) 202 shown in FIG. 13, the inward crests 208 of the scalloped inflow edge 206 are more pronounced (e.g., an amplitude of the wave-like inflow edge 206 is greater than in the other configurations shown in FIGS. 12 and 14). As the frame 52 is expanded further, the inflow edge 206 straightens out, thereby decreasing the amplitudes of the crests 208. For example, in the third expanded configuration (e.g., the over deployed configuration) 204 shown in FIG. 14, the inflow edge 206 is almost completely straightened out, making the crests 208 almost disappear relative to a remainder of the inflow edge 206. In this way, the whip stitches 146 of the skirt allow for stretching of the skirt 102, between the valve's various expanded configurations. This may allow more flexibility in a final, expanded diameter of the valve 100.

Returning to FIG. 4, in some embodiments, the whip stitches 146 can be angled in a same direction around the circumference of the frame 52 (and valve 100).

As shown in FIGS. 4 and 5, both the inner layer 112 and the outer layer 110 of the skirt 102 are arranged on the outer surface 104 of the frame 52. In some embodiments, as shown in FIGS. 3-5, the valve 100 does not have an additional, inner skirt arranged on the inner surface 106 of the frame 52.

For example, as shown in FIG. 5, the skirt 102 is arranged against and along the outer surface 104 of the frame 52 and the leaflets 60 are arranged against and attached to the inner surface 106 of the frame 52. For example, the cusp edge portions of the leaflets 60 can be sutured to struts 72 that generally follow the contour of the cusp edge portions of the leaflets. In some embodiments, the skirt 102 is attached to the struts 72 of the frame 52 via one or more fasteners (e.g., sutures) 148.

In some embodiments, as shown in FIG. 5, a lower portion of the inner layer 112 can be secured to the struts 72 attached to the lower apices 114 via the one or more fasteners 148 (e.g., sutures). For example, as shown in FIG. 5, the one or more fasteners 148 are connected to at least the inner layer 112 and loop around the struts 72, at the apices 114, and/or loop around the apices 114. In some embodiments, an upper (e.g., outflow) portion of the inner layer 112 can be further secured to the struts 72 arranged proximate to the mid-point 142. In some embodiments, additional portions of the inner layer 112 and/or the outer layer 110 can be secured to the struts 72 of the frame 52. In some embodiments, more or less sutures than those shown in FIG. 5 may be used to secure the lower portion of the inner layer 112 to the struts 72.

Figure 6:
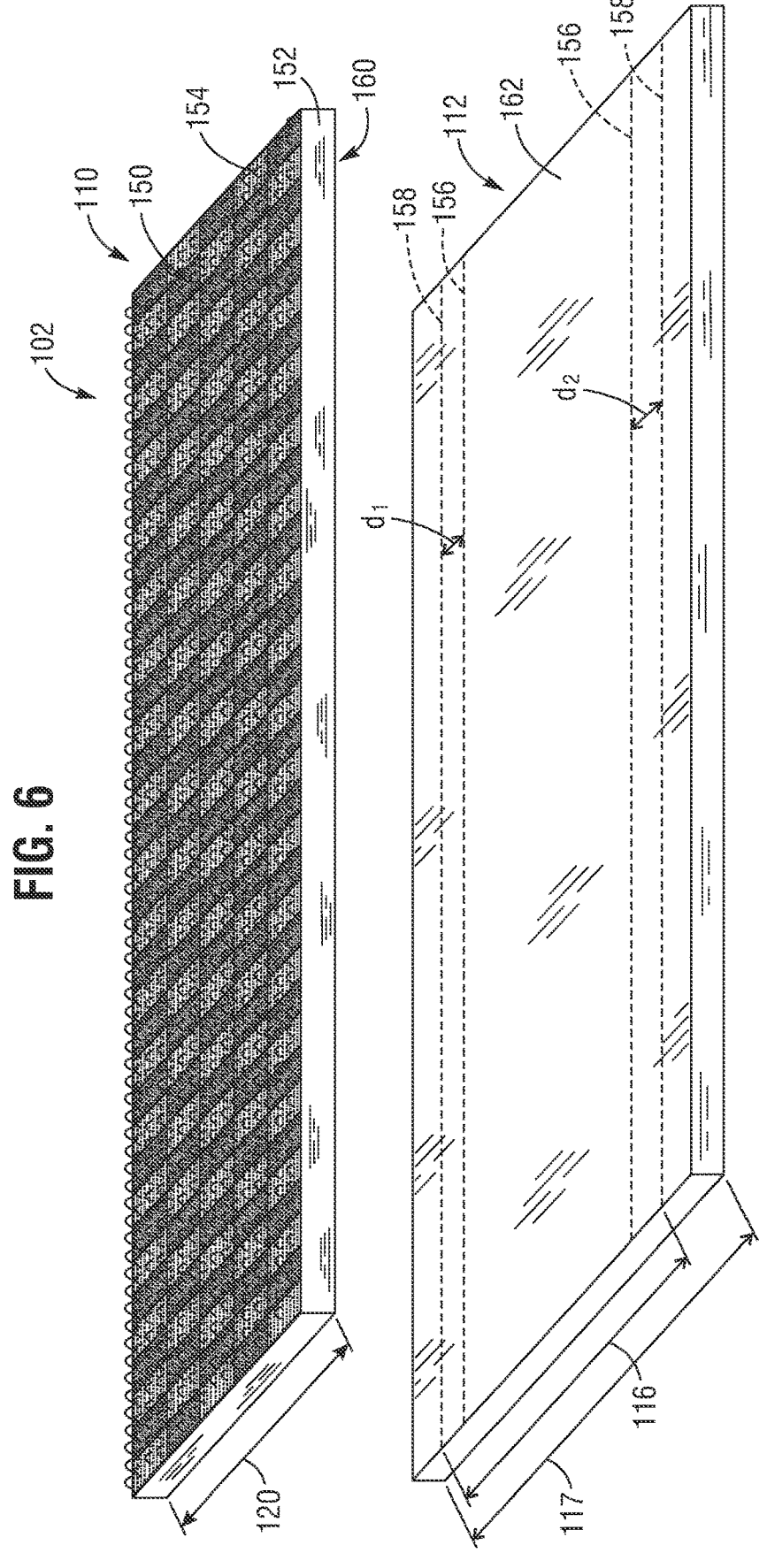
FIG. 6 is a perspective, exploded view of the multi-layer skirt of FIGS. 3-5, prior to the layers of the multi-layer skirt being secured together.

FIG. 6 is a perspective, exploded view of the skirt 102, prior to the outer layer 110 and the inner layer 112 being secured together. The inner layer 112 can be referred to as a woven layer and can comprise a woven material. In some embodiments, the woven material may be a plain woven cloth made of polyethylene terephthalate (PET) fabric (e.g., Dacron). In other embodiments, the woven material of the inner layer 112 can be another type of woven fabric, made up of an implantable polymer, such as Ultra High Molecular Weight Polyethylene (UHMWPE), Polytetrafluoroethylene (PTFE), Polypropylene, thermoplastic polyurethane (TPU), and polyetheretherketone (PEEK), In other embodiments, the woven material of the inner layer 112 can be a different type of weave structure such satin, twill, leno, or another derivative of a plain weave. In some embodiment the woven material of the inner layer 112 can be a cloth that is post treated by calendaring to reduce the thickness of the cloth that can be advantageous for a lower profile and surface modification that may reduce cell attachment, as well as tissue ingrowth and overgrowth. In some embodiments, the woven material of the inner layer 112 can be a cloth that is post treated by applying a thin coating of polymers such as thermoplastic polyurethane (TPU) over the inner surface for surface modification in order to actively resist tissue ingrowth or overgrowth.

In some embodiments, the inner layer 112 can also comprise a film including any of a variety of crystalline or semi-crystalline polymeric materials, such as polytetrafluoroethylene (PTFE), PET, polypropylene, polyamide, polyetheretherketone (PEEK), TPU, etc. In this manner, the inner layer 112 can be relatively thin and yet strong enough to allow the skirt 102 to be sutured to the frame, and to allow the prosthetic heart valve to be crimped, without tearing. Further details on the construction of the fabric of the inner layer 112 are discussed below with reference to FIGS. 10 and 11. In some embodiments, the inner layer 112 can also comprise an electrospun membrane including any of a variety of crystalline or semi-crystalline polymeric materials, such as polytetrafluoroethylene (PTFE), PET, UHMWPE, etc.

In some embodiments, the outer layer 110 can be referred to as a knitted layer and can comprise a knitted material (e.g., knitted fabric). In some embodiments, the knitted material of the of the outer layer 110 can also comprise a knitted PET fabric. In other embodiments, the knitted material can comprise a different type of fiber or yarn (other than PET fiber) such as Nylon, ePTFE, TPU, or the like. In some embodiments, the outer layer 110 can comprise a woven or nonwoven fabric made of PET or the like. As explained further below with reference to FIGS. 7-9, the outer layer 110 can be knitted, woven, or nonwoven in such a way that it comprises an outer soft, plush (e.g., fuzzy) surface 150 and a base surface or layer 152.

For example, the plush surface 150 can be a plush nap or pile of the fabric of the outer layer 110. Exemplary fabrics having a pile include velour, velvet, velveteen, corduroy, terrycloth, fleece, etc. As explained further below with reference to FIGS. 7-9, the base layer 152 can comprise warp and base yarns (e.g., strands, etc.) knitted into a mesh-like structure. As shown in FIG. 6, the pile of the plush surface 150 (second layer) can comprise pile strands or yarn 154 that are knitted into loops and that extend from the base layer 152. These loop-like yarns can help to increase the surface area of the outer layer 110 of the skirt, thereby providing faster sealing against the native tissue, after implantation. In some embodiments, the pile yarns (e.g., loop yarn) 154 can be separate strands/yarns that are incorporated in the base layer 152, as described further below with reference to FIGS. 7-9.

The outer layer 110 can be attached (e.g., by sutures, thread, etc.) to the inner layer 112 via a plurality of whip stitches 146, as explained above with reference to FIG. 4. More specifically, the inner surface 160 of the outer layer 110 can be positioned against the outer surface 162 of the inner layer 112, between dashed lines 156. For example, in FIG. 6, the location of the ends (e.g., ends of end portions 128 and 132) of the outer layer 110 when the outer layer 110 is attached to the inner layer 112, is represented as dashed lines 156 on the inner layer 112. Dashed lines 158 represent the location of where the outermost, axial ends of the inner layer 112 that are positioned against the outer surface of the frame 52 would begin to fold over to extend toward and over the outer, plush surface 150 of the outer layer 110. Said another way, the dashed lines 158 represent where the bends of the folds 122 and 124 are formed on the inner layer 112.

Once the outer layer 110 and inner layer 112 are positioned in face-sharing contact with one another, as described above, they can be attached together via the lines of whip stitches 146, as shown in FIG. 4. In some embodiments, the lines of whip stitches 146 can extend between the outer layer 110 and inner layer 112, along its long dimension (e.g., long dimension shown in FIG. 6), in a region of the dashed lines 156 (e.g., at or inward of dashed lines 156).

As shown in FIG. 6, the upper edge of the inner layer 112 and the upper edge of the outer layer 110 are offset from one another by distance d1 (on the frame 52) to create the tapered, upper, first fold 122 and the lower edge of the inner layer 112 and the lower edge of the outer layer 110 are offset from one another by distance d2 (on the frame 52) to create the tapered, lower, second fold 124. In some embodiments the distances d1 and d2 may be the same. In other embodiments, as shown in FIG. 3, the distance d2 may be longer than the distance d1 to create a longer taper region at the inflow end of the valve.

In some embodiments, once the outer layer 110 is secured to the inner layer 112, the resulting skirt swatch can be folded and sutured into a cylindrical shape. The resulting skirt 102 can then be secured to the frame 52 by attachment means, for example, by suturing, clipping, adhering, etc. it to the struts 72 (e.g., as shown in FIG. 5).

Figure 7:
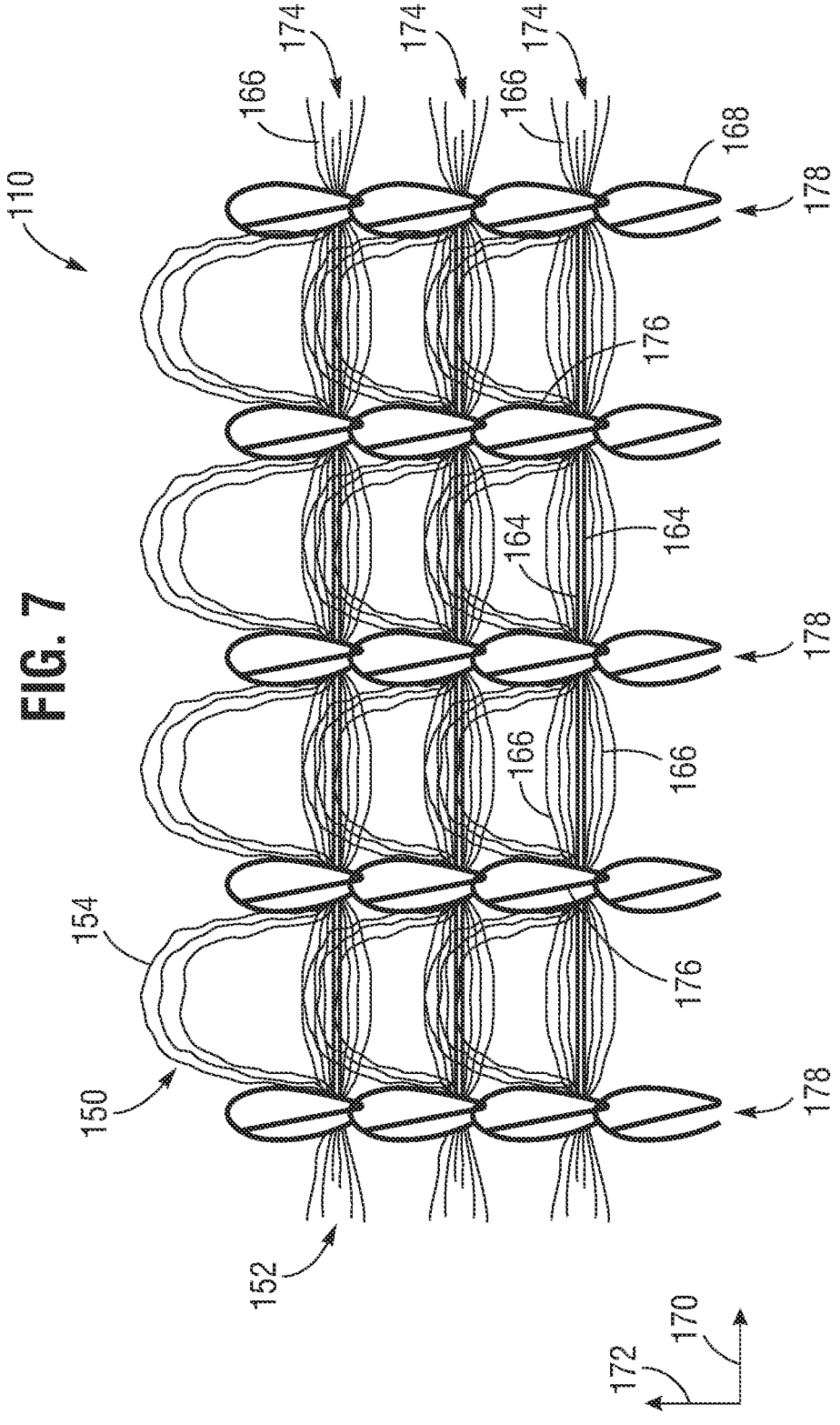
FIG. 7 is a schematic of an exemplary outer layer of a multi-layer skirt, illustrating the different yarn components that are knit together to form the outer layer.
Figure 8:
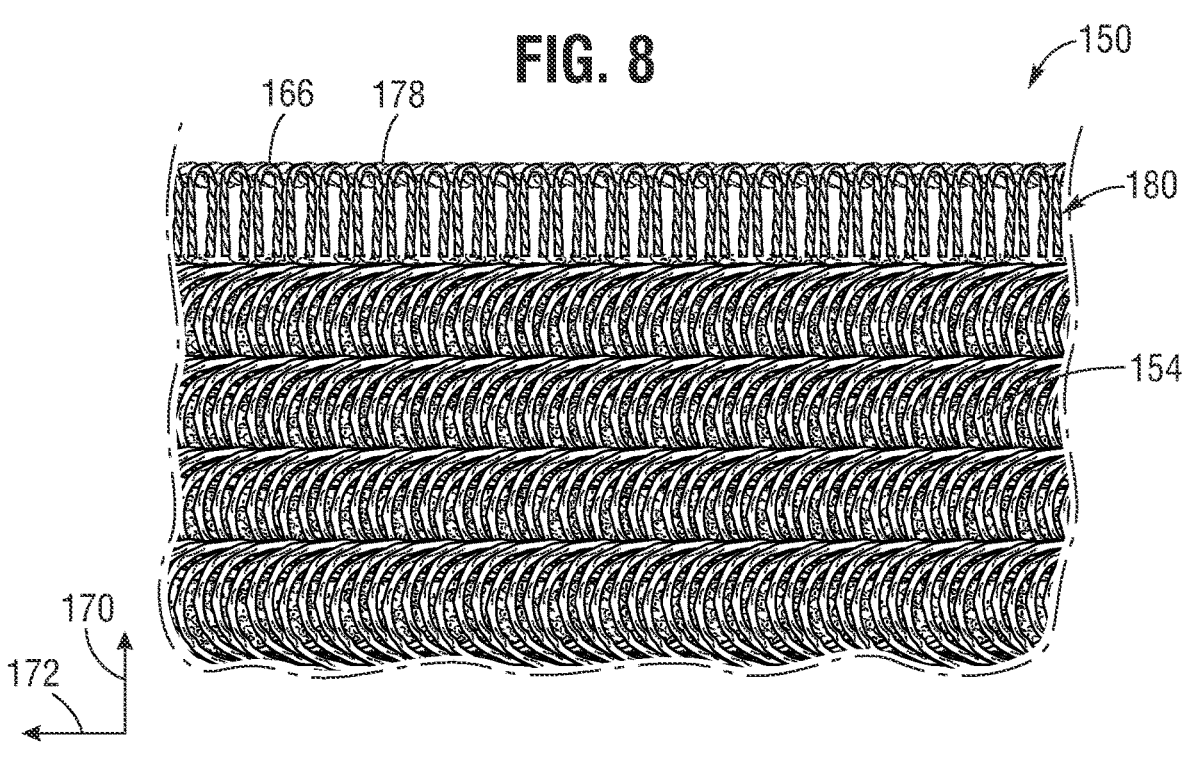
FIG. 8 is a micrograph of a loop side of an exemplary outer layer of a multi-layer skirt.
Figure 9:
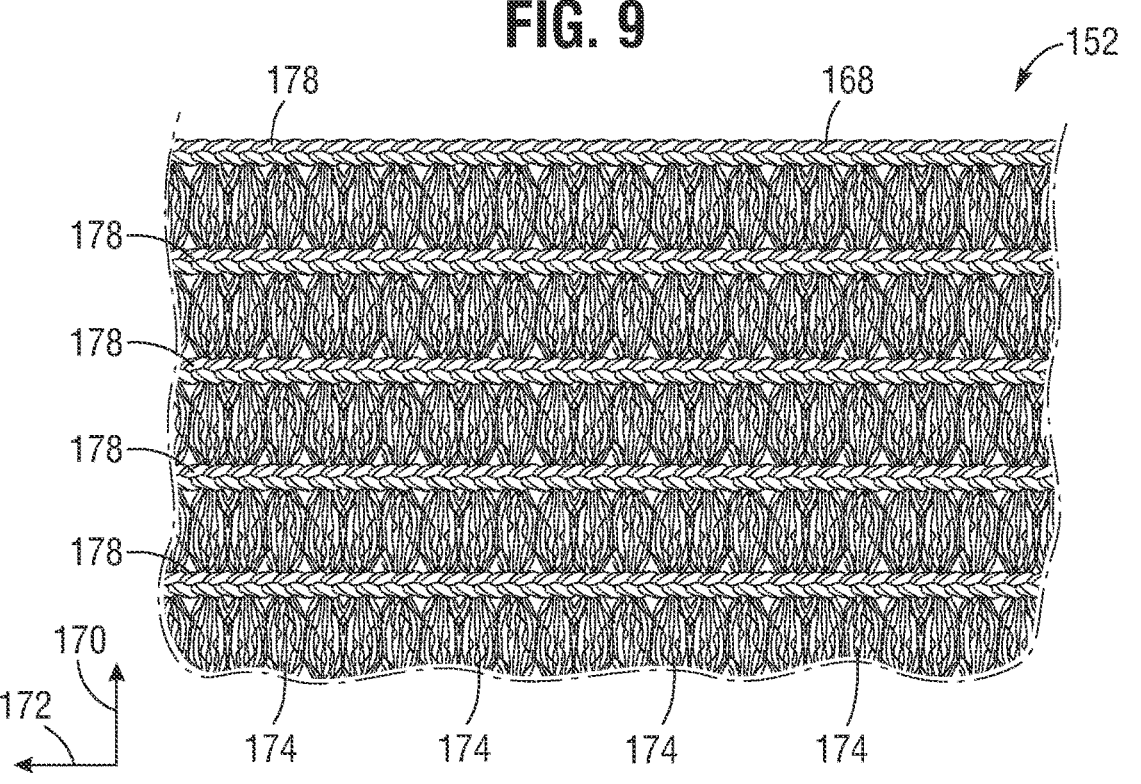
FIG. 9 is a micrograph of a mesh side, or base layer, of the exemplary outer layer of the multi-layer skirt.

FIGS. 7-9 illustrate the cloth construction of the outer layer 110 in more detail, according to one embodiment. Specifically, FIG. 7 shows a schematic of the different yarn components that are knit together to form the plush surface 150 and the base layer 152 of the outer layer 110. As explained further below, the specific knit construction of the outer layer 110 results in the plush surface 150 arranged on one side of the outer layer 110 (e.g., the loop side) and a mesh-like surface (the base layer 152) arranged on the opposite, other side of the outer layer 110 (e.g., the mesh side). Micrographs of an exemplary outer layer fabric constructed according to the schematic of FIG. 7 are shown in FIG. 8 (showing the plush surface, or loop side) and FIG. 9 (showing the base layer or mesh side).

In some embodiments, the outer layer 110 can be constructed as a crochet knitted cloth. In some embodiments, the outer layer 110 can be referred to as a crochet knit velour cloth or fabric due to the yarns and knitting techniques that are used to construct it, as described further below.

Since the outer layer 110 is a knitted fabric or cloth, it comprises a series of courses, each course running in the course direction 170, and a series of wales, each wale running in the wale direction 172. The course direction 170 and wale direction 172 are indicated in FIGS. 7-9, for reference. For example, FIG. 7 shows a portion of the outer layer 110 in an orientation, as it is knit (e.g., constructed), while FIGS. 8 and 9 show a portion of the outer layer 110 in the orientation in which it is arranged on the prosthetic heart valve (e.g., as shown in FIG. 4). For further reference, in FIGS. 8 and 9, the course direction is substantially parallel with the central longitudinal axis 108 of the valve (as shown in FIG. 4).

The outer layer 110 can be knit to a desired width (e.g., in the course direction 170). As a result, the edges of the outer layer 110 do not require laser cutting.

As shown in FIG. 7, the outer layer 110 is constructed from multiple different yarns. In some embodiments, the different yarns may have a different denier, filament count, and/or texture. However, in some embodiments, the different yarns of the outer layer 110 may comprise a same material (e.g., PET).

In FIG. 7, the different yarns of the outer layer 110 include a first base yarn 164, a second base yarn 166, and a warp yarn 168, which are all knit together to form the base layer 152, or mesh side, of the outer layer 110 (as shown in more detail in FIG. 9). For example, as shown in FIG. 7, the first base yarn 164 and the second base yarn 166 are knit together and extend along the course direction, thereby forming a course 174.

Each course 174 is connected to an adjacent course 174 by a warp loop 176 of a series of spaced apart warp loops in the course 174, each warp loop 176 in one course 174 being part of a different wale 178. In FIG. 9, the longitudinal arrangement (relative to the central longitudinal axis of the frame of the valve) of the series of consecutive courses 174 are shown. Further, FIG. 9 shows the horizontal (circumferential direction when arranged on the frame of the valve) arrangement of the series of spaced apart (e.g., spaced apart by a section of each course) wales 178. In this way, the base layer 152, or mesh side, of the outer layer 110 appears as a mesh-like structure.

In some embodiments, as shown in FIG. 7, the first base yarn 164 can comprise a one or more strands/yarns (e.g., one, two, three, or the like) that extend through a central portion of each course 174 while the second base yarn 166 can comprise one or more strands/yarns (e.g., three, four, six, or the like) that extend around or on the outsides of the strands/yarns of the first base yarn 164.

In some embodiments, the strands/yarns of the first base yarn 164 can be twisted strands/yarns with a denier of from about 1 D to about 100 D, about 10 D to about 30 D, or about 15 D to about 25 D and a filament count of from about 8 to about 100 filaments per strand/yarn, about 8 to about 28 filaments per strand/yarn, or about 13 to about 23 filaments per strand/yarn. In other embodiments, the strands/yarns of the first base yarn 164 can be twisted strands/yarns with a denier of about 20 D and a filament count of about 18 filaments per strand/yarn.

In some embodiments, the strands/yarns of the second base yarn 166 can be texturized strands/yarns with a denier of from about 10 D to about 100 D, about 30 D to about 50 D, or about 35 D to about 45 D and a filament count of from about 10 to about 200 filaments per strand/yarn, about 17 to about 37 filaments per strand/yarn, or about 22 to about 32 filaments per strand/yarn. In other embodiments, the strands/yarns of the second base yarn 166 can be texturized strands/yarns with a denier of about 40 D and a filament count of about 27 filaments per strand/yarn. For example, the filaments of the strands/yarns of the second base yarn 166 can be twisted, heat set, and untwisted such that the filaments retain their deformed, twisted shape in the relaxed, non-stretched configuration, thereby making them texturized. In other embodiments, the filaments can be texturized by false-twist or pin texturing, crimping, coiling, or the like.

In some embodiments, the strands/yarns of the warp yarn 168 can be fully drawn yarn (FDY) or a twisted yarn ranging from 2 turns per inch to 16 turns per inch with a denier of from about 1 D to about 50 D, about 10 D to about 30 D, or about 15 D to about 25 D and a filament count of from about 1 to about 50 filaments per strand/yarn, about 7 to about 37 filaments per strand/yarn, or about 13 to about 23 filaments per strand/yarn. In other embodiments, the strands/yarns of the warp yarn 168 can be FDY with a denier of about 20 D and a filament count of about 18 filaments per strand/yarn.

Additionally, in some embodiments, the first and second base yarns 164 and 166 and the warp yarn 168 can be knit with a density of about 17 wales per inch and about 61 courses per inch. In some embodiments, the first and second base yarns 164 and 166 and the warp yarn 168 can be knit with a density in a range of about 14 to about 28 wales per inch and about 40 to about 75 courses per inch.

As introduced above, in some embodiments the strands/yarns of the first and second base yarns 164 and 166 and the warp yarn 168 can be made from, for example, biocompatible thermoplastic polymers such as PET, UHMWPE, Polypropylene, Nylon, ePTFE, PTFE, Polyvinylidene Fluoride (PVDF), PEEK or the like, or other suitable natural or synthetic fibers, or soft monolithic materials.

As shown in FIG. 7, the different yarns of the outer layer 110 further include the pile yarns 154 which are incorporated into the base layer 152. For example, the pile yarns 154 are formed as one or more loops that extend from the first and second base yarns 164 and 166 of the base layer 152. The "loop side" of the outer layer 110, formed from the overlapping loops of the pile yarns 154, is shown in FIG. 8.

As shown in FIG. 8, an upper edge 180 (e.g., the edge arranged closer to the mid-point of the valve when the skirt is arranged on the valve, as shown in FIG. 4, for example) of the outer layer 110 (as well as the lower edge, which is not shown in FIG. 8) does not have the looped pile yarns 154, and instead, includes only the second base yarn 166. This may help to provide the tapered ends in the folds 122 and 124 of the skirt 102. In some embodiments, as shown in FIGS. 7 and 8, the edges of the base layer 152, including the upper edge 180 (which can also be referred to as an outflow edge), includes two times the amount of strands/yarns of the second base yarn 166 in order to strengthen the edges for increased assembly integrity and cloth durability. In alternate embodiments, the upper edge 180 can include the first base yarn 164 and the second base yarn 166, but no pile yarns 154.

In some configurations, the pile yarns 154 are texturized strands/yarns with a denier of from about 10 D to about 150 D or about 19 D to about 21 D and a filament count of from about 10 to about 300 filaments per strand/yarn or about 17 to about 19 filaments per strand/yarn. In other embodiments, the strands/yarns of the pile yarns 154 can be texturized with a denier of about 20 D and a filament count of about 18 filaments per strand/yarn.

In some embodiments, the loops of the pile yarns 154 on the plush surface 150 may have a certain pattern, such that they are not knitted on each wale 178, but they are alternating with a ratio of 1:1 (1 wale of loop and 1 empty wale), 1:2 (1 wale of loop and 2 empty wale), or 2:1, such that the density of the loops on the plush surface 150 is adjusted based upon the size and filament count of the pile yarn 154 used. In some embodiments, the loops of the pile yarns 154 on the plush surface 150 may have a certain pattern, such that they are not knitted on each course, so that different densities of loops are achieved.

In some embodiments, the pile yarns 154 have an increased surface area due to, for example, a wavy or undulating structure (as shown in FIG. 7). In configurations such as the looped pile embodiment of FIGS. 7 and 8, the loop structure and the increased surface area provided by the textured strands or textured yarn of the piles yarns 154 can allow the loops to act as a scaffold for tissue growth into and around the loops of the pile. Promoting tissue growth into the plush surface 150 can increase retention of the valve at the implantation site and contribute to long-term stability of the valve.

The construction of the outer layer 110, as described herein, can also contribute to improved compressibility and shape memory properties of the skirt 102 over known valve coverings and skirts. For example, the pile yarns 154 can be compliant such that the plush surface 150 compresses under load (e.g., when in contact with tissue, implants, or the like), and returns to its original size and shape when the load is relieved. This can help to improve sealing between the plush layer 150 and, for example, the walls of the native annulus. The compressibility provided by the plush surface 150 of the outer layer 110 is also beneficial in reducing the crimp profile of the prosthetic valve.

In some embodiments, the compressed thickness of the outer layer 110 is about 0.8 mm and the uncompressed thickness of the outer layer 110 is about 1.2 mm. In other embodiments, the compressed thickness of the outer layer 110 is in a range of about 0.6 mm to about 1.0 mm and the uncompressed thickness of the outer layer 110 is in a range of about 1.0 mm to about 1.4 mm.

Figure 10:
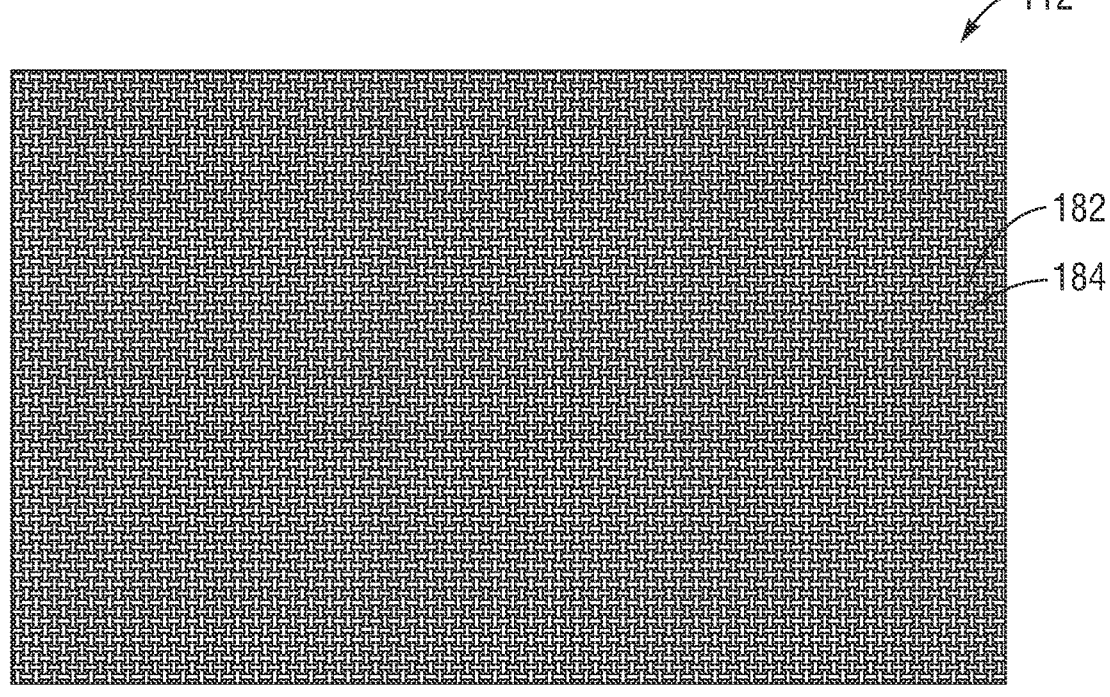
FIG. 10 is a micrograph of an exemplary inner layer of a multi-layer skirt.
Figure 10:
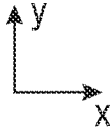
Figure 11:
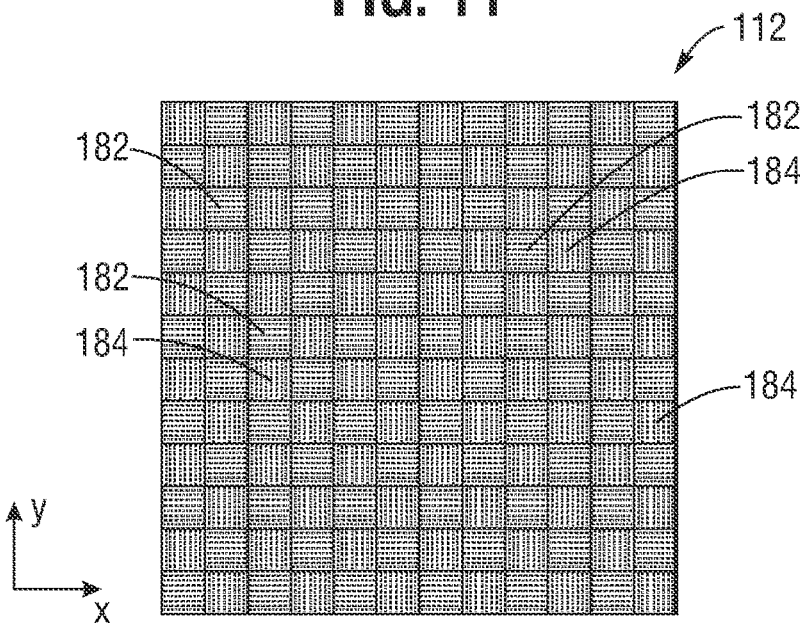
FIG. 11 is a detail view of a portion of the micrograph of FIG. 10, illustrating the woven configuration of the inner layer.
Figures 12, 13, 14:
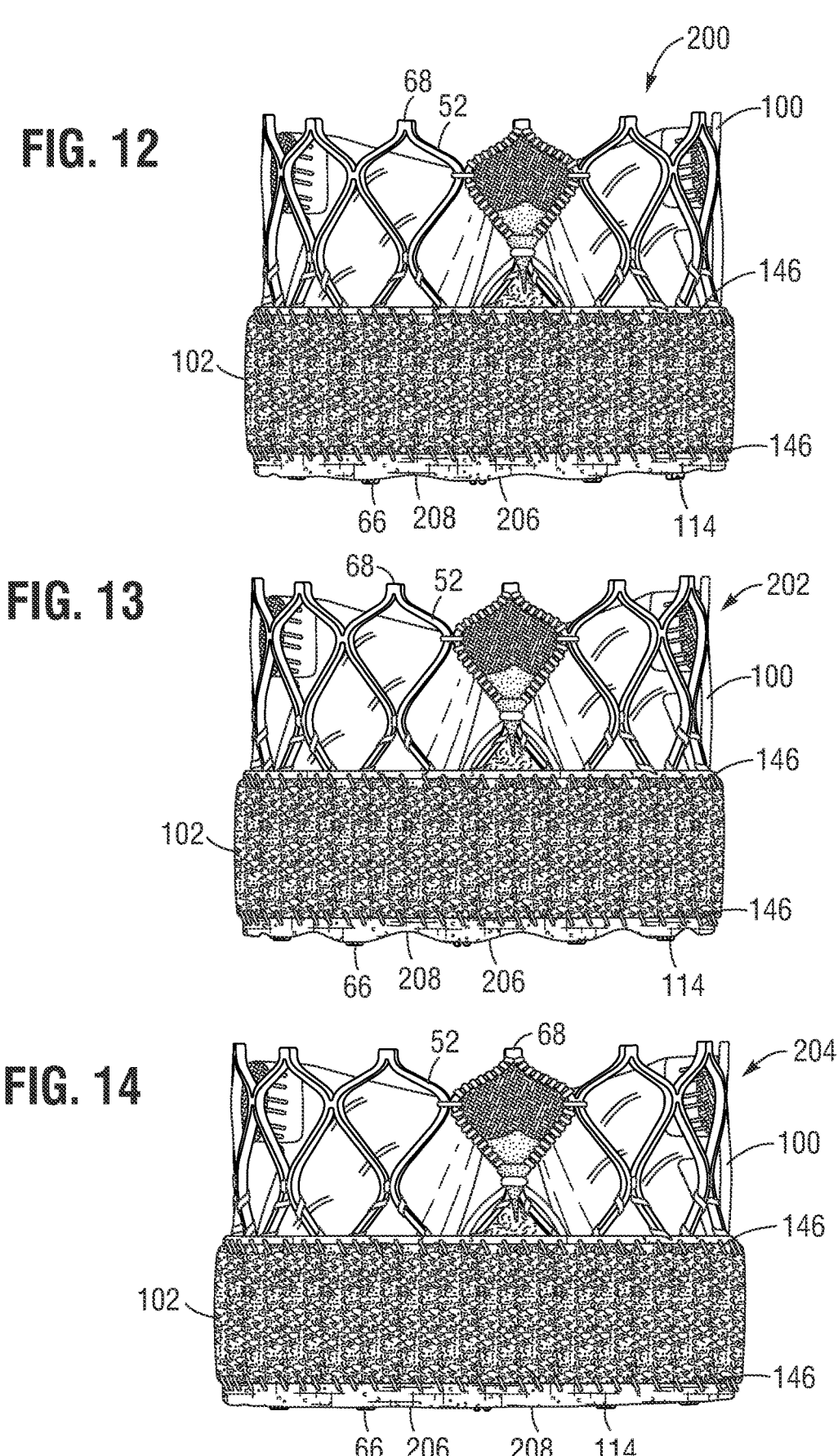
FIG. 12 is a side view of the prosthetic heart valve including the multi-layer skirt of FIG. 4, in a first expanded state where the valve in expanded to its target diameter.
FIG. 13 is a side view of the prosthetic heart valve including the multi-layer skirt of FIG. 4, in a second expanded state where the valve in under deployed relative to the configuration of FIG. 12.
FIG. 14 is a side view of the prosthetic heart valve including the multi-layer skirt of FIG. 4, in a third expanded state where the valve in expanded to an over deployed state relative to the configuration of FIG. 12.

FIGS. 10 and 11 illustrate the cloth construction of the inner layer 112 in more detail. Specifically, FIG. 10 shows an exemplary micrograph of the inner layer 112 while FIG. 11 shows a zoomed-in, detail portion of the micrograph of FIG. 10. As introduced above, the inner layer 112 is a woven cloth or fabric.

As shown in FIGS. 10 and 11, the inner layer 112 can comprise a plurality of first strands 182 (e.g., yarns, etc.) oriented generally along the x-axis and a plurality of second yarns 184 oriented generally along the y-axis. In certain configurations, the second strands/yarns 184 are warp strands/yarns, meaning that during the weaving process the second strands/yarns 184 are held by the loom, while the first strands/yarns 182 are weft strands/yarns, which are interlaced with the warp strands/yarns by a moving shuttle or weft-carrying mechanism during the weaving process. However, in some embodiments the first strands/yarns 182 can be warp strands/yarns and the second strands/yarns 184 can be weft strands/yarns.

Each of the first strands/yarns 182 and the second strands/yarns 184 can comprise a plurality of constituent filaments that are spun, wound, twisted, intermingled, interlaced, or the like, together to form the respective strands/yarns.

In some embodiments, the first strands/yarns 182 have a denier of from about 1 D to about 100 D, about 10 D to about 50 D, about 10 D to about 30 D, or about 15 D to about 25 D. In some embodiments, the first strands/yarns 182 have a filament count of from about 1 to about 300 filaments per strand/yarn, about 10 to about 100 filaments per strand/yarn, about 10 to about 50 filaments per strand/yarn, about 10 to about 30 filaments per strand/yarn, or about 10 to about 28 filaments per strand/yarn. In some embodiments, the first strands/yarns 182 have a denier of about 20 D and a filament count of about 18 filaments per strand/yarn. In some embodiments, the first strands/yarns 182 can also be flat (e.g., non-twisted) strands/yarns. However, in alternate embodiments, the first strands/yarns 182 can comprise twisted and/or texturized filaments.

The second strands/yarns 184 can be twisted strands/yarns comprising a plurality of twisted filaments. In alternate embodiments, the second strands/yarn can comprise flat (non-twisted) or texturized filaments. In some embodiments, the second strands/yarns 184 have a denier of from about 1 D to about 100 D, about 10 D to about 50 D, about 10 D to about 30 D, or about 15 D to about 25 D. In some embodiments, the second strands/yarns 184 have a filament count of from about 1 to about 100 filaments per strand/yarn, about 10 to about 100 filaments per strand/yarn, about 10 to about 50 filaments per strand/yarn, about 10 to about 30 filaments per strand/yarn, or about 10 to about 28 filaments per strand/yarn. In some embodiments, the second strands/yarns 184 have a denier of about 20 D and a filament count of about 18 filaments per strand/yarn.

The first strands/yarns 182 and the second strands/yarns 184 can be woven together to form the inner layer 112. For example, the first and second strands/yarns 182 and 184 can be woven together in a plain weave pattern in which the first strands/yarns 182 (e.g., the weft strands/yarns) pass over a second strand/yarn 184 (e.g., a warp yarn) and then under the next second strand/yarn 184 in a repeating pattern. This weave pattern is illustrated in detail in FIG. 10.

In some embodiments, the density of the first strands/yarns 182 is from about 10 strands/yarns per inch to about 500 strands/yarns per inch, about 50 strands/yarns per inch to about 200 strands/yarns per inch, or about 100 strands/yarns per inch to about 200 strands/yarns per inch. In some embodiments, the density of the first strands/yarns 182 is about 160 strands/yarns per inch.

In some embodiments, the density of the second strands/yarns 184 is from about 10 strands/yarns per inch to about 500 strands/yarns per inch, about 50 strands/yarns per inch to about 200 strands/yarns per inch, or about 100 strands/yarns per inch to about 200 strands/yarns per inch. In some embodiments, the density of the second strands/yarns 184 is about 170 strands/yarns per inch.

In alternate embodiments, other weave patterns (e.g., other than the plain weave pattern) can be used, such as over two under two, over two under one, etc. The first woven portions can also be woven in plain weave derivative patterns such as twill, satin, or combinations of any of these.

In some embodiments, the first and second strands/yarns 182 and 184 can comprise any of various biocompatible thermoplastic polymers such as PET, Nylon, ePTFE, UHMWPE, etc., or other suitable natural or synthetic fibers. For example, in some embodiments, the first and second strands/yarns 182 and 184 can comprise PET strands/yarns.

In certain embodiments, the inner layer 112 can be woven on a loom, and can then be heat-treated or heat-set to achieve the desired size and configuration. For example, depending upon the material selected, heat-setting can cause the inner layer 112 to shrink. In some embodiments, heat-setting can also cause a texturizing effect, or increase the amount of texturizing, of the strands/yarns.

In some embodiments a thickness of the resulting inner layer 112 can be from about 10 to about 150 μm, about 20 to about 100 μm, or about 40 to about 80 μm. In some embodiments, the thickness of the resulting inner layer 112 can be about 60 μm.

In some embodiments, the resulting cloth of the inner layer 112 can be calendared. Calendaring the inner layer 112 can include pressing the cloth under a pair of heated rollers to reduce a thickness of the cloth. Calendaring the inner layer 112 may result in a lower overall crimp profile of the prosthetic heart valve including the skirt 102. In these embodiments, the resulting thickness of the inner layer 112 can be in a range of about 1 to about 30 μm or about 5 to about 15 μm. In some embodiments, the thickness of the calendared inner layer 112 can be about 10 μm.

The inner layer 112 can then be attached to the outer layer 110, as described above with reference to FIGS. 3-6.

The inner layer 112 can provide protection to the leaflets of the prosthetic heart valve from the protruding pile yarns of the outer layer 110. As a result, reduced abrasion to the leaflets may occur and a longevity of the leaflets may be increased. Further, the woven, inner layer 112 can reduce or inhibit tissue growth, thereby further protecting the leaflets and increasing their longevity.

In contrast, the plush outer surface of the outer layer 110 can promote tissue growth and increase the speed at which the valve seals against the native tissue of the heart after implantation.

Constructing a two-layer skirt, as described herein, allows for knitting the outer layer as a narrow ribbon, to the desired width, thereby eliminating a need for laser cutting the knitted cloth to a desired size. The knit construction described herein may also reduce or eliminate the risk of an open edge that may be susceptible to unravelling (and the production of particulates from laser-cut molten polymer or cut fibers). Thus, the knit construction of the outer layer of the skirt can drastically improve the edge quality of the skirt, which could potentially interact with the leaflets. As a result, degradation to the leaflets is reduced and a longevity and integrity of the leaflets may be increased. Further, by using more than two yarns in the base layer of the knit, outer layer, the knit structure of the skirt is made more robust against unravelling or particulates.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A prosthetic heart valve, comprising: a frame comprising a plurality of struts, the frame being radially collapsible and expandable between a collapsed configuration and an expanded configuration, the frame having an inflow end and an outflow end; at leaflet structure situated at least partially within the frame; and a sealing member disposed around an outer surface of the frame, the sealing member comprising: an inner layer comprising a woven fabric; and an outer layer comprising a knitted fabric, the knitted fabric comprising a base layer including a plurality of courses formed from a first base yarn and a second base yarn that are knit together and a plurality of wales formed from a warp yarn, where each loop of the warp yarn is knit together with the first base yarn and second base yarn of two adjacent courses; wherein the inner layer is arranged against the outer surface of the frame and the outer layer is arranged against and attached to the inner layer and wherein the inner layer is folded over at either end, in an axial direction relative to a central longitudinal axis of the frame, to form folds that overlap respective ends of the outer layer.

Example 2. The prosthetic heart valve of any example herein, particularly example 1, wherein the outer layer further comprises a plurality of pile yarns that are knit into loops and that extend outward from the base layer to form a plush outer surface of the outer layer.

Example 3. The prosthetic heart valve of any example herein, particularly example 2, wherein edges of the outer layer extending around a circumference of the frame and arranged on opposite ends of the outer layer, the opposite ends arranged along the axial direction, do not include any pile yarns of the plurality of pile yarns and wherein a thickness of the outer layer is smaller at the edges than a remainder of the outer layer that includes the plurality of pile yarns.

Example 4. The prosthetic heart valve of any example herein, particularly example 3, wherein the edges of the outer layer include only the second base yarn.

Example 5. The prosthetic heart valve of any example herein, particularly example 3, wherein the folds are created at opposite ends of the sealing member, the opposite ends arranged along the axial direction, each fold including a narrower, first portion where the inner layer folds over itself and a wider, second portion where the inner layer overlaps an outer surface of an end portion of the outer layer, and wherein each fold is tapered in an outward axial direction, from the second portion to the first portion.

Example 6. The prosthetic heart valve of any example herein, particularly example 2, wherein the pile yarns are texturized yarns having a denier in a range of 10 D to 150 D and a filament count in a range of 10 to 300 filaments per yarn.

Example 7. The prosthetic heart valve of any example herein, particularly example 2, wherein the pile yarns are texturized yarns having a denier in a range of 19 D to 21 D and a filament count in a range of 17 to 19 filaments per yarn.

Example 8. The prosthetic heart valve of any example herein, particularly any one of examples 1-7, wherein the first base yarn and the second base yarn have one or more of a different denier, a different filament count, and a different yarn type, the different yarn type including one of a flat, texturized, or twisted yarn.

Example 9. The prosthetic heart valve of any example herein, particularly any one of examples 1-8, wherein the first base yarn has a denier in a range of 15 D to 25 D and a filament count in a range of 13 to 23 filaments per yarn.

Example 10. The prosthetic heart valve of any example herein, particularly any one of examples 1-9, wherein the second base yarn has a denier in a range of 35 D to 45 D and a filament count in a range of 22 to 32 filaments per yarn.

Example 11. The prosthetic heart valve of any example herein, particularly any one of examples 1-10, wherein the first base yarn is twisted and the second base yarn is texturized.

Example 12. The prosthetic heat valve of any example herein, particularly any one of examples 1-11, wherein the warp yarn is a fully drawn yarn.

Example 13. The prosthetic heart valve of any example herein, particularly any one of examples 1-12, wherein the warp yarn has a denier in a range of 15 D to 25 D and a filament count in a range of 13 to 23 filaments per yarn.

Example 14. The prosthetic heart valve of any example herein, particularly any one of examples 1-13, wherein the woven fabric of the inner layer and the knitted fabric of the outer layer each comprise polyethylene terephthalate (PET) yarns.

Example 15. The prosthetic heart valve of any example herein, particularly any one of examples 1-14, wherein the inner layer and outer layer are attached to one another via a plurality of whip stitches.

Example 16. The prosthetic heart valve of any example herein, particularly example 15, wherein the plurality of whip stitches includes a first line of whip stitches that secure the inner layer and the outer layer together at an axial location where the inner layer overlaps an outer surface of the inner layer at a first end of the sealing member arranged at the inflow end of the frame and a second line of whip stitches that secure the inner layer and the outer layer together at an axial location where the inner layer overlaps an outer surface of the inner layer at a second end of the sealing member arranged closer to a mid-point of the frame than the inflow end, the mid-point arranged between the inflow end and the outflow end.

Example 17. The prosthetic heart valve of any example herein, particularly any one of examples 1-16, wherein a length of the outer layer, in the axial direction, is shorter than a length of the inner layer and wherein ends of the outer layer are offset from respective ends of the inner layer.

Example 18. The prosthetic heart valve of any example herein, particularly example 17, wherein the inner layer extends on the frame from the inflow end to a mid-point arranged between the inflow end and outflow end.

Example 19. The prosthetic heart valve of any example herein, particularly example 18, wherein the outer layer extends on the inner layer from an axial position that is spaced away from the inflow end to an axil position that is arranged proximate to the mid-point, but spaced away from and short of the mid-point.

Example 20. The prosthetic heart valve of any example herein, particularly example 17, wherein the folds are tapered folds arranged on opposite ends of the sealing member, in the axial direction, wherein a first tapered fold is formed by a first end of the inner layer folding over itself and then extending inward, in the axial direction, to overlap a first end of the outer layer, and wherein a second tapered fold is formed by a second end of the inner layer folding over itself and then extending inward to overlap a second end of the outer layer.

Example 21. The prosthetic heart valve of any example herein, particularly any one of examples 1-20, wherein the first base yarn, the second base yarn, and the warp yarn are knit together with a density in a range of 14 to 28 wales per inch and 40 to 75 courses per inch.

Example 22. The prosthetic heart valve of any example herein, particularly any one of examples 1-21, wherein the inner layer comprises a plurality of warp yarns and a plurality of weft yarns that are woven together.

Example 23. The prosthetic heart valve of any example herein, particularly example 22, wherein the plurality of warp yarns are twisted yarns and the plurality of weft yarns are flat yarns.

Example 24. A prosthetic heart valve, comprising: a frame comprising a plurality of struts, the frame being radially collapsible and expandable between a collapsed configuration and an expanded configuration, the frame having an inflow end and an outflow end; at leaflet structure situated at least partially within the frame; and a sealing member disposed around an outer surface of the frame, the sealing member extending in an axial direction from the inflow end to a mid-point of the frame, the axial direction relative to a central longitudinal axis of the frame, the mid-point arranged between the inflow end and outflow end, the sealing member comprising: an inner layer comprising a woven fabric; and an outer layer comprising a knitted fabric, the knitted fabric comprising a base layer formed from a first base yarn and a second base yarn that are knit together and a plush outer surface formed from a plurality of pile yarns that are knit into loops and that extend outward from the base layer; wherein the inner layer is arranged against the outer surface of the frame and the outer layer is arranged against and attached to the inner layer and wherein the inner layer is folded over at both ends of the sealing member, the ends arranged opposite one another along the axial direction, to form folds that overlap respective ends of the outer layer.

Example 25. The prosthetic heart valve of any example herein, particularly example 24, wherein the base layer is further formed from a warp yarn that is knit together with the first base yarn and the second base yarn to form a plurality wales of the base layer that are spaced apart from one another, wherein the first base yarn and the second base yarn form a plurality of courses of the base layer, and wherein each course is connected to an adjacent course by a warp loop of each wale.

Example 26. The prosthetic heart valve of any example herein, particularly example 25, wherein the warp yarn is a fully drawn yarn, the first base yarn is a twisted yarn, and the second base yarn is a texturized yarn.

Example 27. The prosthetic heart valve of any example herein, particularly any one of examples 25 and 26, wherein the spaced apart wales and the courses of the base layer form a mesh-like, inner surface of the outer layer which is arranged in face-sharing contact with an outer surface of the inner layer.

Example 28. The prosthetic heart valve of any example herein, particularly any one of examples 25-27, wherein the warp yarn has a denier in a range of 15 D to 25 D and a filament count in a range of 13 to 23 filaments per yarn.

Example 29. The prosthetic heart valve of any example herein, particularly any one of examples 25-28, wherein the first base yarn, the second base yarn, and the warp yarn are knit together with a density in a range of 14 to 28 wales per inch and 40 to 75 courses per inch.

Example 30. The prosthetic heart valve of any example herein, particularly any one of examples 24-29, wherein the pile yarns have a denier in a range of 10 D to 150 D and a filament count in a range of 10 to 300 filaments per yarn.

Example 31. The prosthetic heart valve of any example herein, particularly any one of examples 24-30, wherein the first base yarn and the second base yarn have one or more of a different denier, a different filament count, and a different yarn type, the different yarn type being one of a texturized or twisted yarn.

Example 32. The prosthetic heart valve of any example herein, particularly any one of examples 24-31, wherein the first base yarn has a denier in a range of 15 D to 25 D and a filament count in a range of 13 to 23 filaments per yarn.

Example 33. The prosthetic heart valve of any example herein, particularly any one of examples 24-32, wherein the second base yarn has a denier in a range of 35 D to 45 D and a filament count in a range of 22 to 32 filaments per yarn.

Example 34. The prosthetic heart valve of any example herein, particularly any one of examples 24-33, wherein the plurality of pile yarns are compliant and the plush surface is configured to compress under load, wherein the outer layer has a compressed thickness in a range of 0.6 mm to 1.0 mm, and wherein the outer layer has an uncompressed thickness in a range of 1.0 mm to 1.4 mm.

Example 35. The prosthetic heart valve of any example herein, particularly any one of examples 24-34, wherein a first fold of the sealing member is formed at the mid-point, the first fold including a narrower portion formed by two overlapping layers of the inner layer and a wider portion formed by overlapping layers of the outer layer and inner layer, the inner layer overlapping a first end portion of the outer layer, and wherein a second fold of the sealing member is formed at the inflow end, the second fold including a narrower portion formed by two overlapping layers of the inner layer and a wider portion formed by overlapping layers of the outer layer and inner layer, the inner layer overlapping a second end portion of the outer layer.

Example 36. The prosthetic heart valve of any example herein, particularly example 35, wherein the first end portion of the outer layer is offset, in the axial direction, from a first end of the sealing member formed by a first folded over end of the inner layer, at the mid-point, and wherein the second end portion of the outer layer is offset, in the axial direction, from a second end of the sealing member formed by a second folded over end of the inner layer, at the inflow end.

Example 37. The prosthetic heart valve of any example herein, particularly any one of examples 35 and 36, wherein edges of the outer layer arranged at the first end portion and the second end portion do not include pile yarns of the plurality of pile yarns and have a smaller thickness than a remainder of the outer layer.

Example 38. The prosthetic heart valve of any example herein, particularly any one of examples 24-37, wherein the inner layer and outer layer are attached to one another via a plurality of whip stitches.

Example 39. The prosthetic heart valve of any example herein, particularly any one of examples 24-38, wherein the sealing member is attached to the plurality of struts via a plurality of fasteners.

Example 40. The prosthetic heart valve of any example herein, particularly any one of examples 24-39, wherein the inner layer comprises a plurality of warp yarns and a plurality of weft yarns that are woven together.

Example 41. The prosthetic heart valve of any example herein, particularly example 40, wherein the plurality of warp yarns and the plurality of weft yarns are woven together in a plain weave pattern.

Example 42. The prosthetic heart valve of any example herein, particularly any one of examples 24-41, wherein the woven fabric of the inner layer and the knitted fabric of the outer layer each comprise polyethylene terephthalate (PET) yarns.

Example 43. A prosthetic heart valve, comprising: a frame comprising a plurality of struts, the frame being radially collapsible and expandable between a collapsed configuration and an expanded configuration, the frame having an inflow end and an outflow end; at leaflet structure situated at least partially within the frame; and a sealing member disposed around an outer surface of the frame, the sealing member extending in an axial direction from the inflow end to a mid-point of the frame, the axial direction relative to a central longitudinal axis of the frame, the mid-point arranged between the inflow end and outflow end, the sealing member comprising: an inner layer comprising a woven fabric; and an outer layer comprising a knitted fabric, the knitted fabric comprising: a base layer including a plurality of courses formed from a first base yarn and a second base yarn that are knit together and a plurality of wales formed from a warp yarn, where each loop of the warp yarn is knit together with the first base yarn and second base yarn of two adjacent courses; and a plush outer surface formed from a plurality of pile yarns that are knit into loops and that extend outward from the base layer; wherein the inner layer is arranged against the outer surface of the frame and the outer layer is arranged against and attached to the inner layer and wherein the inner layer is folded over at either end of the sealing member to form tapered folds, each tapered fold overlapping a respective end of the outer layer at a wider portion of the tapered fold.

Example 44. The prosthetic heart valve of any example herein, particularly example 43, wherein each tapered fold tapers from the wider portion, formed by three overlapping layers of the inner layer and outer layer, to a narrower portion formed by two overlapping layers of the inner layer, the narrower portion arranged at one of a first end of the sealing member arranged at the mid-point and a second end of the sealing member arranged at the inflow end.

Example 45. The prosthetic heart valve of any example herein, particularly any one of examples 43-44, wherein end portions of the outer layer are narrower than a remainder of the outer layer and do not include any pile yarns of the plurality of pile yarns.

Example 46. The prosthetic heart valve of any example herein, particularly any one of examples 43-45, wherein the inner layer and outer layer are attached to one another via a plurality of whip stitches, the plurality of whip stitches extending around a circumference of the frame, at either end of the sealing member where the inner layer overlaps the outer layer.

Example 47. The prosthetic heart valve of any example herein, particularly any one of examples 43-46, wherein the first base yarn and the second base yarn have one or more of a different denier, a different filament count, and a different yarn type, the different yarn type including one of a texturized or twisted yarn.

Example 48. The prosthetic heart valve of any example herein, particularly any one of examples 43-47, wherein the woven fabric of the inner layer and the knitted fabric of the outer layer each comprise polyethylene terephthalate (PET) yarns.

Example 49. The prosthetic heart valve of any example herein, particularly any one of examples 43-48, wherein the inner layer comprises a plurality of warp yarns and a plurality of weft yarns that are woven together in a plain weave pattern.

Example 50. The prosthetic heart valve of any example herein, particularly any one of examples 43-49, wherein a length of the sealing member is shorter than a length of the frame and wherein a length of the outer layer of the sealing member is shorter than the length of the sealing member, the lengths arranged in the axial direction.

Example 51. The prosthetic heart valve of any example herein, particularly any one of examples 43-50, wherein leaflets of the leaflet structure are arranged on an inner surface of the frame and face an inner side of the inner layer of the sealing member.

Example 52. A prosthetic heart valve, comprising: a frame comprising a plurality of struts, the frame being radially collapsible and expandable between a collapsed configuration and an expanded configuration, the frame having an inflow end and an outflow end; at leaflet structure situated at least partially within the frame; and a sealing member disposed around an outer surface of the frame, the sealing member comprising: an inner layer; and a plush outer layer comprising a plush outer surface; wherein the inner layer is arranged against the outer surface of the frame and the outer layer is arranged against and attached to the inner layer and wherein the inner layer is folded over at outflow and inflow ends of the inner layer, in an axial direction relative to a central longitudinal axis of the frame, to overlap respective ends of the outer layer and form tapered folds at opposite ends of the sealing member, each tapered fold including a narrower, first portion where the inner layer folds over and contacts itself and a wider, second portion where the inner layer overlaps an outer surface of an end portion of the outer layer.

Example 53. The prosthetic heart valve of any example herein, particularly example 52, wherein the outer layer comprises a knitted fabric with the plush outer surface, the knitted fabric comprising a base layer including a plurality of courses formed from a first base yarn and a second base yarn that are knit together and a plurality of wales formed from a warp yarn, where each loop of the warp yarn is knit together with the first base yarn and second base yarn of two adjacent courses.

Example 54. The prosthetic heart valve of any example herein, particularly example 53, wherein the outer layer further comprises a plurality of pile yarns that are knit into loops and that extend outward from the base layer to form a plush outer surface of the outer layer.

Example 55. The prosthetic heart valve of any example herein, particularly example 54, wherein edges of the outer layer extending around a circumference of the frame and arranged on opposite ends of the outer layer, the opposite ends arranged along the axial direction, do not include any pile yarns of the plurality of pile yarns and wherein a thickness of the outer layer is smaller at the edges than a remainder of the outer layer that includes the plurality of pile yarns.

Example 56. The prosthetic heart valve of any example herein, particularly example 55, wherein the edges of the outer layer include only the second base yarn.

Example 57. The prosthetic heart valve of any example herein, particularly example 54, wherein the pile yarns are texturized yarns having a denier in a range of 10 D to 150 D and a filament count in a range of 10 to 300 filaments per yarn.

Example 58. The prosthetic heart valve of any example herein, particularly any one of examples 53-57, wherein the first base yarn and the second base yarn have one or more of a different denier, a different filament count, and a different yarn type, the different yarn type including one of a flat, texturized, or twisted yarn.

Example 59. The prosthetic heart valve of any example herein, particularly any one of examples 53-58, wherein the first base yarn has a denier in a range of 15 D to 25 D and a filament count in a range of 13 to 23 filaments per yarn and wherein the second base yarn has a denier in a range of 35 D to 45 D and a filament count in a range of 22 to 32 filaments per yarn.

Example 60. The prosthetic heart valve of any example herein, particularly any one of examples 53-59, wherein the first base yarn is twisted and wherein the second base yarn is texturized.

Example 61. The prosthetic heart valve of any example herein, particularly any one of examples 53-60, wherein the warp yarn has a denier in a range of 15 D to 25 D and a filament count in a range of 13 to 23 filaments per yarn.

Example 62. The prosthetic heart valve of any example herein, particularly any one of examples 53-61, wherein the first base yarn, the second base yarn, and the warp yarn are knit together with a density in a range of 14 to 28 wales per inch and 40 to 75 courses per inch and wherein the inner layer comprises a plurality of warp yarns and a plurality of weft yarns that are woven together in a plain weave pattern.

Example 63. The prosthetic heart valve of any example herein, particularly any one of examples 52-62, wherein the inner layer comprises a woven fabric and the outer layer comprises a knitted fabric and wherein the woven fabric of the inner layer and the knitted fabric of the outer layer each comprise polyethylene terephthalate (PET) yarns.

Example 64. The prosthetic heart valve of any example herein, particularly any one of examples 52-63, wherein the inner layer and outer layer are attached to one another via a plurality of whip stitches and wherein the plurality of whip stitches includes a first line of whip stitches that secure the inner layer and the outer layer together at an axial location where the inner layer overlaps an outer surface of the inner layer at a first end of the sealing member arranged at the inflow end of the frame and a second line of whip stitches that secure the inner layer and the outer layer together at an axial location where the inner layer overlaps an outer surface of the inner layer at a second end of the sealing member arranged closer to a mid-point of the frame than the inflow end, the mid-point arranged between the inflow end and the outflow end.

Example 65. The prosthetic heart valve of any example herein, particularly any one of examples 52-64, wherein a length of the outer layer, in the axial direction, is shorter than a length of the inner layer, wherein ends of the outer layer are offset from respective ends of the inner layer, and wherein each tapered fold is tapered in an outward axial direction, from the second portion to the first portion.

In view of the many possible embodiments to which the principles of the disclosed technology may be applied, it should be recognized that the illustrated embodiments are only preferred examples of the disclosed technology and should not be taken as limiting the scope of the claimed subject matter. Rather, the scope of the claimed subject matter is defined by the following claims and their equivalents.

We claim:

1. A prosthetic heart valve, comprising:
   a frame comprising a plurality of struts, the frame being radially collapsible and expandable between a collapsed configuration and an expanded configuration, the frame having an inflow end and an outflow end;
   at leaflet structure situated at least partially within the frame; and
   a sealing member disposed around an outer surface of the frame, the sealing member comprising:
      an inner layer; and
      a plush outer layer comprising a plush outer surface;
      wherein the inner layer is arranged against the outer surface of the frame and the outer layer is arranged against and attached to the inner layer and wherein the inner layer is folded over at inflow and outflow ends of the inner layer, in an axial direction relative to a central longitudinal axis of the frame, to overlap respective ends of the outer layer and form tapered folds at opposite ends of the sealing member, each tapered fold including a narrower, first portion where the inner layer folds over and contacts itself and a wider, second portion where the inner layer overlaps an outer surface of an end portion of the outer layer.

2. The prosthetic heart valve of claim 1, wherein the outer layer comprises a knitted fabric with the plush outer surface, the knitted fabric comprising a base layer including a plurality of courses formed from a first base yarn and a second base yarn that are knit together and a plurality of wales formed from a warp yarn, where each loop of the warp yarn is knit together with the first base yarn and second base yarn of two adjacent courses.

3. The prosthetic heart valve of claim 2, wherein the outer layer further comprises a plurality of pile yarns that are knit into loops and that extend outward from the base layer to form a plush outer surface of the outer layer.

4. The prosthetic heart valve of claim 3, wherein edges of the outer layer extending around a circumference of the frame and arranged on opposite ends of the outer layer, the opposite ends arranged along the axial direction, do not include any pile yarns of the plurality of pile yarns and wherein a thickness of the outer layer is smaller at the edges than a remainder of the outer layer that includes the plurality of pile yarns.

5. The prosthetic heart valve of claim 4, wherein the edges of the outer layer include only the second base yarn.

6. The prosthetic heart valve of claim 3, wherein the pile yarns are texturized yarns having a denier in a range of 10 D to 150 D and a filament count in a range of 10 to 300 filaments per yarn.

7. The prosthetic heart valve of claim 2, wherein the first base yarn and the second base yarn have one or more of a different denier, a different filament count, and a different yarn type, the different yarn type including one of a flat, texturized, or twisted yarn.

8. The prosthetic heart valve of claim 2, wherein the first base yarn has a denier in a range of 15 D to 25 D and a filament count in a range of 13 to 23 filaments per yarn and wherein the second base yarn has a denier in a range of 35 D to 45 D and a filament count in a range of 22 to 32 filaments per yarn.

9. The prosthetic heart valve of claim 2, wherein the first base yarn is twisted and wherein the second base yarn is texturized.

10. The prosthetic heart valve of claim 2, wherein the warp yarn has a denier in a range of 15 D to 25 D and a filament count in a range of 13 to 23 filaments per yarn.

11. The prosthetic heart valve of claim 2, wherein the first base yarn, the second base yarn, and the warp yarn are knit together with a density in a range of 14 to 28 wales per inch and 40 to 75 courses per inch and wherein the inner layer comprises a plurality of warp yarns and a plurality of weft yarns that are woven together in a plain weave pattern.

12. The prosthetic heart valve of claim 1, wherein the inner layer comprises a woven fabric and the outer layer comprises a knitted fabric and wherein the woven fabric of the inner layer and the knitted fabric of the outer layer each comprise polyethylene terephthalate (PET) yarns.

13. The prosthetic heart valve of claim 1, wherein the inner layer and outer layer are attached to one another via a plurality of whip stitches and wherein the plurality of whip stitches includes a first line of whip stitches that secure the inner layer and the outer layer together at an axial location where the inner layer overlaps an outer surface of the inner layer at a first end of the sealing member arranged at the inflow end of the frame and a second line of whip stitches that secure the inner layer and the outer layer together at an axial location where the inner layer overlaps an outer surface of the inner layer at a second end of the sealing member arranged closer to a mid-point of the frame than the inflow end, the mid-point arranged between the inflow end and the outflow end.

14. The prosthetic heart valve of claim 1, wherein a length of the outer layer, in the axial direction, is shorter than a length of the inner layer, wherein ends of the outer layer are offset from respective ends of the inner layer, and wherein each tapered fold is tapered in an outward axial direction, from the second portion to the first portion.

15. A prosthetic heart valve, comprising:
a frame comprising a plurality of struts, the frame being radially collapsible and expandable between a collapsed configuration and an expanded configuration, the frame having an inflow end and an outflow end;
at leaflet structure situated at least partially within the frame; and
a sealing member disposed around an outer surface of the frame, the sealing member extending in an axial direction from the inflow end to a mid-point of the frame, the axial direction relative to a central longitudinal axis of the frame, the mid-point arranged between the inflow end and outflow end, the sealing member comprising:
an inner layer comprising a woven fabric; and
an outer layer comprising a knitted fabric, the knitted fabric comprising a base layer formed from a first base yarn and a second base yarn that are knit together and a plush outer surface formed from a plurality of pile yarns that are knit into loops and that extend outward from the base layer;
wherein the inner layer is arranged against the outer surface of the frame and the outer layer is arranged against and attached to the inner layer and wherein the inner layer is folded over at both ends of the sealing member, the ends arranged opposite one another along the axial direction, to form folds that overlap respective ends of the outer layer.

16. The prosthetic heart valve of claim 15, wherein the base layer is further formed from a warp yarn that is knit together with the first base yarn and the second base yarn to form a plurality wales of the base layer that are spaced apart from one another, wherein the first base yarn and the second base yarn form a plurality of courses of the base layer, and wherein each course is connected to an adjacent course by a warp loop of each wale.

17. The prosthetic heart valve of claim 16, wherein the warp yarn is a fully drawn yarn, the first base yarn is a twisted yarn, and the second base yarn is a texturized yarn.

18. The prosthetic heart valve of claim 16, wherein the spaced apart wales and the courses of the base layer form a mesh-like, inner surface of the outer layer which is arranged in face-sharing contact with an outer surface of the inner layer.

19. The prosthetic heart valve of claim 15, wherein the plurality of pile yarns are compliant and the plush outer surface is configured to compress under load, wherein the outer layer has a compressed thickness in a range of 0.6 mm to 1.0 mm, and wherein the outer layer has an uncompressed thickness in a range of 1.0 mm to 1.4 mm.

20. The prosthetic heart valve of claim 15, wherein a first fold of the sealing member is formed at the mid-point, the first fold including a narrower portion formed by two overlapping layers of the inner layer and a wider portion formed by overlapping layers of the outer layer and inner layer, the inner layer overlapping a first end portion of the outer layer, wherein a second fold of the sealing member is formed at the inflow end, the second fold including a narrower portion formed by two overlapping layers of the inner layer and a wider portion formed by overlapping layers of the outer layer and inner layer, the inner layer overlapping a second end portion of the outer layer, and wherein edges of the outer layer arranged at the first end portion and the second end portion do not include pile yarns of the plurality of pile yarns and have a smaller thickness than a remainder of the outer layer.

21. A prosthetic heart valve, comprising:
a frame comprising a plurality of struts, the frame being radially collapsible and expandable between a collapsed configuration and an expanded configuration, the frame having an inflow end and an outflow end;
at leaflet structure situated at least partially within the frame; and
a sealing member disposed around an outer surface of the frame, the sealing member extending in an axial direction from the inflow end to a mid-point of the frame, the axial direction relative to a central longitudinal axis of the frame, the mid-point arranged between the inflow end and outflow end, the sealing member comprising:
an inner layer comprising a woven fabric; and
an outer layer comprising a knitted fabric, the knitted fabric comprising:
a base layer including a plurality of courses formed from a first base yarn and a second base yarn that are knit together and a plurality of wales formed from a warp yarn, where each loop of the warp yarn is knit together with the first base yarn and second base yarn of two adjacent courses; and
a plush outer surface formed from a plurality of pile yarns that are knit into loops and that extend outward from the base layer;

wherein the inner layer is arranged against the outer surface of the frame and the outer layer is arranged against and attached to the inner layer and wherein the inner layer is folded over at either end of the sealing member to form tapered folds, each tapered fold overlapping a respective end of the outer layer at a wider portion of the tapered fold.

22. The prosthetic heart valve of claim 21, wherein each tapered fold tapers from the wider portion, formed by three overlapping layers of the inner layer and outer layer, to a narrower portion formed by two overlapping layers of the inner layer, the narrower portion arranged at one of a first end of the sealing member arranged at the mid-point and a second end of the sealing member arranged at the inflow end.

23. The prosthetic heart valve of claim 21, wherein end portions of the outer layer are narrower than a remainder of the outer layer and do not include any pile yarns of the plurality of pile yarns.

* * * * *